US012753235B2

(12) United States Patent
Takayama et al.

(10) Patent No.: US 12,753,235 B2
(45) Date of Patent: Oct. 6, 2026

(54) FC-BINDING PROTEIN HAVING IMPROVED ACID STABILITY, PRODUCTION METHOD FOR SAID PROTEIN, AND ANTIBODY-ADSORBING AGENT USING SAID PROTEIN

(71) Applicant: TOSOH CORPORATION, Yamaguchi (JP)

(72) Inventors: Masumi Takayama, Kanagawa (JP); Yosuke Terao, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 1354 days.

(21) Appl. No.: 16/971,431

(22) PCT Filed: Feb. 21, 2019

(86) PCT No.: PCT/JP2019/006640
§ 371 (c)(1),
(2) Date: Aug. 20, 2020

(87) PCT Pub. No.: WO2019/163919
PCT Pub. Date: Aug. 29, 2019

(65) Prior Publication Data

US 2021/0002367 A1 Jan. 7, 2021

(30) Foreign Application Priority Data

Feb. 22, 2018 (JP) ................................ 2018-029994
Aug. 20, 2018 (JP) ................................ 2018-154007
Jan. 11, 2019 (JP) ................................ 2019-003038

(51) Int. Cl.
*C07K 14/705* (2006.01)
*C07K 1/14* (2006.01)
*C07K 16/28* (2006.01)
*C12N 15/10* (2006.01)
*C12N 15/64* (2006.01)

(52) U.S. Cl.
CPC .............. *C07K 16/283* (2013.01); *C07K 1/14* (2013.01); *C12N 15/64* (2013.01)

(58) Field of Classification Search
CPC .................... C07K 16/283; C07K 1/14; C07K 14/70535; C07K 17/00; C12N 15/64; C12N 15/1058
See application file for complete search history.

(56) References Cited

U.S. PATENT DOCUMENTS 8,658,766 B2 * 2/2014 Birks ............... C07K 14/70535 435/325
11,414,475 B2 * 8/2022 Hatayama ............ C07K 16/065
2013/0079499 A1 * 3/2013 Hatayama ................ C07K 1/22 530/410
2016/0222081 A1 8/2016 Asaoka et al.
2017/0218044 A1 8/2017 Asaoka et al.

FOREIGN PATENT DOCUMENTS

JP 2017-178908 A 10/2017
WO 2011/111393 A1 9/2011
WO 2015/041303 A1 3/2015
WO 2015/199154 A1 12/2015
WO WO-2018056374 A1 * 9/2017
WO 2018/151817 A2 8/2018

OTHER PUBLICATIONS

Takai, T., Jpn. "Role of Fcy Receptors in Immune Regulation and Diseases", J. Clin. Immunol., 28, 2005, pp. 318-326.
Galon, J. et al., "Affinity of the interaction between Fc gamma receptor type III (FcyRIII) and monomeric human IgG subclasses. Role of FcyRIII glycosylation" Eur. J. Immunol., 27, 1997, pp. 1928-1932.
Richards, J.O. et al., "Optimization of antibody binding to FcyRlla enhances macrophage phagocystosis oftumor cells", Mol. Cancer Ther., 7, 2008, pp. 2517-2527.
Menendez-Arias, L. et al., "Engineering protein thermal stability: Sequence statistics point to residue substitutions in alpha-helices", J. Mol. Biol., vol. 206, 1989, pp. 397-406.
International Search Report issued in International Patent Application No. PCT/JP2019/006640, dated May 21, 2019 and English Translation thereof.

* cited by examiner

*Primary Examiner* — Shafiqul Haq
*Assistant Examiner* — Nam P Nguyen
(74) *Attorney, Agent, or Firm* — Greenblum & Bernstein, P.L.C.

(57) ABSTRACT

An Fc-binding protein having at least amino acid residues of the extracellular domain of the amino acid sequence of wildtype human FcγRIIa (UniProt Accession Number: P12318) wherein the amino acid residues in the domain have an amino acid substitution or deletion at at least a specific position, a method for producing the protein, and an antibody adsorbent using the protein.

10 Claims, 1 Drawing Sheet

Specification includes a Sequence Listing.

FC-BINDING PROTEIN HAVING IMPROVED ACID STABILITY, PRODUCTION METHOD FOR SAID PROTEIN, AND ANTIBODY-ADSORBING AGENT USING SAID PROTEIN

FIELD

The present invention relates to an Fc-binding protein having binding affinity to immunoglobulin G (IgG). More specifically, the present invention relates to an Fc-binding protein with improved acid stability compared to wild-type Fcγ receptor-11a, obtained by substituting an amino acid residue with another amino acid residue or by deleting an amino acid residue at a specific position of a human Fcγ receptor-11a, a method for producing the protein, and an antibody adsorbent obtained by immobilizing the protein on an insoluble carrier.

BACKGROUND

Fc receptors are receptor proteins that bind to the Fc region of immunoglobulin molecules and perform intracellular signaling on binding to an antigen-immunoglobulin immune complex (NPL 1). The particularly important Fcγ receptor (FcγR), which binds to the immunoglobulin G (IgG), can be subdivided into the following subgroups: FcγRI (CD64), FcγRIIa (CD32a), FcγRIIb (CD32b), FcγRIIc (CD32c), FcγRIIIa (CD16a) and FcγRIIIb (CD16b) (NPL 1 and 2). Binding of the IgG immune complex to FcγR occurs due to binding of the Fc region of IgG to the FcγR. Each type of FcγR molecule has an IgG Fc region recognition domain which recognizes one type of IgG or IgGs belonging to the same subclass. This determines which accessory cells are recruited for individual immune responses (NPL 1 and 2).

Among the FcγRs, FcγRIIa is present on macrophages, neutrophils, etc., and is involved in ADCP (antibody-dependent cellular phagocytosis) action which is an important human immune mechanism (NPL 3). The amino acid sequence of human FcγRIIa (SEQ ID NO: 1) is registered in public databases such as UniProt (Accession Number: P12318). Furthermore, the functional domain, the signal peptide sequence for traversing the cell membrane, and the position of the transmembrane domain of the human FcγRIIa structure are similarly publicly available. FIG. 1 shows a schematic structure of FcγRIIa. Note that the amino acid numbers in FIG. 1 correspond to the amino acid numbers set forth in SEQ ID NO: 1. That is, in SEQ ID NO: 1, the methionine at position 1 to the serine at position 33 constitute a signal sequence (S), the glutamine at position 34 to the glycine at position 217 constitute an extracellular domain (EC), the isoleucine at position 218 to the tyrosine at position 240 constitute a transmembrane domain (TM), and the cysteine at position 241 to the asparagine at position 317 constitute an intracellular domain (C).

In order to make the FcγRIIa industrially applicable, it is preferable for the acid stability thereof to be high in view of use, storage, and the like. However, there has heretofore been no attempt to improve acid stability of human FcγRIIa.

CITATION LIST

Patent Literature

[NPL 1] Takai T., Jpn. J. Clin. Immunol., 28, 318-326, 2005

[NPL 2] J. Galon et al., Eur. J. Immunol., 27, 1928-1932, 1997

[NPL 3] J. O. Richards et al., Mol. Cancer Ther., 7, 2517-2527, 2008

SUMMARY

Technical Problem

The object of the present invention is to provide an Fc-binding protein with improved acid stability compared to wild type human FcγRIIa, a method for producing the protein, and an antibody adsorbent using the protein.

Solution to Problem

As a result of extensive research carried out by the present inventors to achieve the above object, the amino acid residues involved in improving acid stability in human FcγRIIa were identified and variants in which an amino acid residue was substituted with another amino acid or was deleted were found to have excellent acid stability. Thereby the present invention was achieved.

Specifically, the present application encompasses the following embodiments [1] to [13].

[1] An Fc-binding protein selected from (I) to (IV) below:

(I) an Fc-binding protein comprising at least amino acid residues from glutamine at position 29 to glutamine at position 201 of the amino acid sequence set forth in SEQ ID NO: 2, provided the Fc-binding protein has at least any one of the substitutions and deletion indicated in (1) to (12) below in the amino acid residues from position 29 to position 201, (1) a substitution of leucine to serine at position 190 of SEQ ID NO: 2, (2) a substitution of isoleucine to threonine at position 45 of SEQ ID NO: 2, (3) a substitution of glutamine to leucine at position 69 of SEQ ID NO: 2, (4) a substitution of proline to leucine at position 83 of SEQ ID NO: 2, (5) a substitution of threonine to proline at position 123 of SEQ ID NO: 2, (6) a substitution of proline to glutamine at position 42 of SEQ ID NO: 2, (7) a substitution of proline to leucine at position 63 of SEQ ID NO: 2, (8) a substitution of asparagine to serine at position 75 of SEQ ID NO: 2, (9) a substitution of leucine to histidine at position 163 of SEQ ID NO: 2,

(10) a substitution of aspartic acid to valine at position 179 of SEQ ID NO: 2,

(11) a substitution of isoleucine to valine at position 198 of SEQ ID NO: 2,

(12) a deletion of serine at position 62 of SEQ ID NO: 2;

(II) an Fc-binding protein comprising at least amino acid residues from glutamine at position 29 to glutamine at position 201 of the amino acid sequence set forth in SEQ ID NO: 2, provided the Fc-binding protein has at least any one of the substitutions and deletion indicated in (1) to (12) in the amino acid residues from position 29 to position 201, further has any one or more of a substitution, deletion, insertion, and addition of one or several amino acid residues at one or several positions, other than the substitutions and deletion indicated in (1) to (12), and has antibody binding activity;

(III) an Fc-binding protein comprising at least amino acid residues from glutamine at position 29 to glutamine at position 201 of the amino acid sequence set forth in SEQ ID NO: 2, provided the Fc-binding protein has a 70% or more homology with the amino acid sequence from position 29 to position 201, has at least any one of the substitutions and deletion indicated in (1) to (12), and has antibody binding activity;

(IV) an Fc binding protein comprising an amino acid sequence having a 70% or more homology with the entirety of an amino acid sequence having at least any one of the substitutions and deletion indicated in (1) to (12) in amino acid residues from glutamine at position 29 to glutamine at position 201 of the amino acid sequence set forth in SEQ ID NO: 2, retaining the at least any one of the substitutions and deletion, and having antibody binding activity.

[2] The Fc-binding protein according to [1], comprising at least the amino acid substitution indicated in (1) below:

(1) a substitution of leucine to serine at position 190 of SEQ ID NO: 2.

[3] The Fc-binding protein according to [1] or [2], further comprising at least amino acid substitutions at the 6 positions indicated below:

a substitution of isoleucine to valine at position 68 of SEQ ID NO: 2, a substitution of histidine to glutamine at position 80 of SEQ ID NO: 2, a substitution of serine to threonine at position 84 of SEQ ID NO: 2, a substitution of asparagine to threonine at position 90 of SEQ ID NO: 2, a substitution of asparagine to serine at position 91 of SEQ ID NO: 2, a substitution of histidine to arginine at position 125 of SEQ ID NO: 2.

[4] The Fc-binding protein according to [1] or [2] selected from (iv) to (vi) below:

(iv) an Fc binding protein comprising at least amino acid residues from glutamine at position 29 to glutamine at position 201 of an amino acid sequence set forth in any of SEQ ID NOs: 5, 7, 13, 17, 19, 23, and 25;

(v) an Fc binding protein comprising at least amino acid residues from glutamine at position 29 to glutamine at position 201 of an amino acid sequence set forth in any of SEQ ID NOs: 5, 7, 13, 17, 19, 23, and 25, provided the Fc binding protein further has any one or more of a substitution, deletion, insertion, and addition of one or several amino acid residues at one or several positions, other than a substitution of the amino acid sequence, and has antibody binding activity;

(vi) an Fc binding protein comprising at least amino acid residues from glutamine at position 29 to glutamine at position 201 of an amino acid sequence set forth in any of SEQ ID NOs: 5, 7, 13, 17, 19, 23, and 25, provided the Fc-binding protein has a 70% or more homology with the amino acid sequence from position 29 to position 201, retains a substitution of the amino acid sequence, and has antibody binding activity.

[5] The Fc-binding protein according to any one of [1] to [3] selected from (vii) to (ix) below:

(vii) an Fc binding protein comprising at least amino acid residues from glutamine at position 29 to glutamine at position 200 of the amino acid sequence set forth in SEQ ID NO: 35;

(viii) an Fc binding protein comprising at least amino acid residues from glutamine at position 29 to glutamine at position 200 of the amino acid sequence set forth in SEQ ID NO: 35, provided the Fc binding protein further has any one or more of a substitution, deletion, insertion, and addition of one or several amino acid residues at one or several positions, other than a substitution of the amino acid sequence, in the amino acid residues from position 29 to position 200, and has antibody binding activity;

(ix) an Fc binding protein comprising at least amino acid residues from glutamine at position 29 to glutamine at position 200 of the amino acid sequence set forth in SEQ ID NO: 35, provided the Fc-binding protein has a 70% or more homology with the amino acid sequence from position 29 to position 200 and has antibody binding activity.

[6] The Fc-binding protein according to any one of [1] to [3] selected from (x) to (xii) below:

(x) an Fc binding protein comprising at least amino acid residues from glutamine at position 29 to glutamine at position 196 of the amino acid sequence set forth in SEQ ID NO: 43;

(xi) an Fc binding protein comprising at least amino acid residues from glutamine at position 29 to glutamine at position 196 of the amino acid sequence set forth in SEQ ID NO: 43, provided the Fc binding protein further has any one or more of a substitution, deletion, insertion, and addition of one or several amino acid residues at one or several positions, other than a substitution of the amino acid sequence, in the amino acid residues from position 29 to position 196, and has antibody binding activity;

(xii) an Fc binding protein comprising at least amino acid residues from position 29 to position 196 of the amino acid sequence set forth in SEQ ID NO: 43, provided the Fc binding protein has a 70% or more homology with the amino acid sequence from position 29 to position 196, retains an amino acid substitution of the amino acid sequence, and has antibody binding activity.

[7] A polynucleotide encoding the Fc-binding protein according to any one of [1] to [6].

[8] An expression vector comprising the polynucleotide according to [7].

[9] A transformant obtainable by transforming a host with the recombinant vector according to [8] and capable of producing an Fc-binding protein.

[10] The transformant according to [9], wherein the host is *Escherichia coli*.

[11] A method for producing an Fc binding protein, comprising the steps of: producing an Fc binding protein by culturing the transformant according to [9] or [10]; and harvesting the Fc binding protein from the obtained culture product.

[12] An antibody adsorbent obtainable by immobilizing the Fc-binding protein according to any one of [1] to [6] on an insoluble carrier.

[13] An antibody separation method comprising the steps of: adding a solution containing an antibody to a column filled with the adsorbent according to [12] and adsorbing the antibody to the adsorbent; and eluting the antibody adsorbed to the adsorbent using an eluent.

The present invention will be described in detail below.

The Fc binding protein of the present invention is a protein having antibody Fc region-binding properties and comprising at least the amino acid residues from the glutamine at position 29 to the glutamine at position 201 of a polypeptide comprising a wild type human FcγRIIa extracellular domain consisting of the amino acid sequence set forth in SEQ ID NO: 2, provided the protein has at least one amino acid substitution or deletion at a specific position in the amino acid residues from position 29 to position 201. Note that in SEQ ID NO: 2, position 1 to position 26 constitute a MalE signal peptide (oligopeptide consisting of the amino acid residues from position 1 to position 26 of UniProt No. POAEX9), the methionine at position 27 and the glycine at position 28 constitute a linker sequence, position 29 to position 201 constitute the FcγRIIa extracellular domain (the region from position 34 to position 206 in SEQ ID NO: 1), position 202 and position 203 constitute a glycine linker, and position 204 to position 209 constitute a histidine tag. Thus, the Fc-binding protein of the present invention may comprise the entirety or a part of the extracellular domain N-terminal side signal peptide domain or may comprise the entirety or a part of the extracellular domain C-terminal side transmembrane domain and the extracellular domain.

Specifically, the amino acid substitution or deletion in a specific position is at least any one of Pro42Gln (this represents a substitution of proline to glutamine at position 42 of SEQ ID NO: 2 (position 47 in SEQ ID NO: 1), this also applies to the following), Pro63Leu, Asn75Ser, Leu163His, Asp179Val, Leu190Ser, Ile198Val, Ile45Thr, Gln69Leu, Pro83Leu, Thr123Pro, and a deletion of Ser62. Thereamong, a preferable embodiment of the Fc-binding protein of the present invention is an Fc-binding protein comprising at least a Leu190Ser amino acid substitution since the Leu190Ser amino acid substitution particularly improves acid stability.

It is satisfactory for the Fc-binding protein of the present invention to have at least one amino acid substitution or deletion at the above specific position, and provided antibody binding activity is exhibited, may further include at least one of a substitution, deletion, insertion, or addition of an amino acid residue, in addition to the above amino acid substitutions at the specified positions. Specific examples of this embodiment include Fc-binding proteins having antibody binding activity indicated in (i) to (v) below. In cases where an amino acid residue is deleted, a deletion that removes a loop region in the protein secondary structure improves heat resistance and is thus preferable (Manandez-Alias and P. Argos, J. Mol. Biol., 206, 1989).

(i) an Fc-binding protein having the amino acid substitution and/or deletion at the above specific position and further having the following amino acid substitutions, Ile68Val, His80Gln, Ser84Thr, Asn90Thr, Asn91Ser and His125Arg, (ii) an Fc binding protein having the amino acid substitution and/or deletion at the above specific position and further having at least any one or more of a substitution, deletion, insertion, and addition of one or several amino acid residues at one or several positions, (iii) an Fc-binding protein having the amino acid substitution and/or deletion at the above specific position, and the following amino acid substitutions, Ile68Val, His80Gln, Ser84Thr, Asn90Thr, Asn91Ser and His125Arg, and further having at least any one or more of a substitution, deletion, insertion, and addition of one or several amino acid residues at one or several positions, (iv) an Fc-binding protein having an amino acid sequence having 70% or more homology with an amino acid sequence of a polypeptide having the above amino acid substitution and/or deletion at the specific position and retaining the above amino acid substitution and/or deletion at the specific position, (v) an Fc-binding protein having an amino acid sequence having 70% or more homology with an amino acid sequence of a polypeptide having the amino acid substitution and/or deletion at the above specific position and the following amino acid substitutions, Ile68Val, His80Gln, Ser84Thr, Asn90Thr, Asn91Ser and His125Arg, and retaining the amino acid substitution and/or deletion at the above specific position and the following amino acid substitutions, Ile68Val, His80Gln, Ser84Thr, Asn90Thr, Asn91Ser and His125Arg.

The amino acid substitutions, Ile68Val, His80Gln, Ser84Thr, Asn90Thr, Asn91Ser, and His125Arg, set forth in (i), (iii) and (v) are amino acid substitutions for improving heat stability and productivity in recombinant transformants (WO2018/056374). Thus, by further including amino acid substitutions (Ile68Val, His80Gln, Ser84Thr, Asn90Thr, Asn91Ser, and His125Arg) at the six positions in the Fc-binding protein of the present invention having the at least one acid substitution in the specific position, an Fc-binding protein with improved acid stability, heat stability, and productivity in recombinant transformants compared to wild type FcγRIIa can be obtained.

In (ii) and (iii), "one or several" differs depending on the type or position of the amino acid residue on the three-dimensional structure of the protein but refers to, for example, 1 to 50, 1 to 40, 1 to 30, 1 to 20, or 1 to 10. In (ii) and (iii) "at least one or more of a substitution, deletion, insertion, and addition" includes naturally occurring mutants or variants based on individual differences or differences between species of the microorganism from which the gene is derived.

In (iv) and (v), the amino acid sequence homology of 70% or more is satisfactory but the sequence homology may be more (e.g., 80 or more, 85 or more, 90 or more, or 95 or more).

The Fc-binding protein of the present invention may also have conservative amino acid substitutions wherein either or both of the physical and chemical properties of both amino acids are similar. It is known by a person skilled in the art that, generally, without being limited to Fc-binding proteins, proteins which have undergone a conservative substitution retain the function of the proteins which have not undergone the conservative substitution. Examples of conservative substitutions include substitutions between glycine and alanine, aspartic acid and glutamic acid, serine and proline, or glutamic acid and alanine (Protein Structure and Function, Medical Science International, 9, 2005).

Further, the Fc-binding protein of the present invention may further have an oligopeptide added to the N-terminal side or C-terminal side thereof which is useful for separating the protein from a solution containing contaminants. The oligopeptide may be polyhistidine, polylysine, polyarginine, polyglutamic acid, or polyaspartic acid. Further, the Fc-binding protein of the present invention may further have, added thereto on the N-terminal side or C-terminal side thereof, an oligopeptide containing cysteine which is useful for immobilization of the Fc-binding protein of the present invention to a solid phase such as a support for chromatography. The length of oligopeptides added to the N-terminal or C-terminal side of the Fc-binding protein is not particularly limited provided the stability of the Fc-binding protein and the ability thereof to bind IgG are not impaired. When adding an oligopeptide to the Fc-binding protein of the present invention, a method well known to a person skilled in the art may be used to add the oligopeptide by means of genetic engineering using a previously created polynucleotide encoding the oligopeptide to the N-terminal or C-terminal side of the Fc-binding protein. Alternatively, a chemically synthesized oligopeptide may be chemically bonded to the N-terminal or C-terminal side of the Fc-binding protein of the present invention. Further, a signal peptide for effectively promoting expression in a host cell can be added to the N-terminal side of the Fc-binding protein of the present invention. Examples of the signal peptide when *E. coli* is the host include PelB, DsbA, MalE (the region from position 1 to position 26 of the amino acid sequence set forth in UniProt No. P0AEX9), and TorT which are signal peptides that secrete proteins in the periplasm (Japanese Unexamined Patent Publication (Kokai) No. 2011-097898).

Preferred embodiments of the Fc-binding protein of the present invention include Fc-binding proteins containing at least a polypeptide consisting of any of the amino acid sequences indicated in (a) to (i) below. These Fc-binding proteins are preferable in terms of improved acid stability (acid resistance).

(a) FcγRIIa-m7 (the amino acid residues from position 29 to position 201 of the amino acid sequence set forth in SEQ ID NO: 5)

A polypeptide comprising the amino acid residues from the glutamine at position 29 to the glutamine at position 201 of the amino acid sequence set forth in SEQ ID NO: 2, provided the polypeptide has the following amino acid substitutions in the amino acid residues from position 29 to position 201: Ile68Val, His80Gln, Ser84Thr, Asn90Thr, Asn91Ser, His125Arg, and Leu190Ser.

(b) FcγRIIa-m1 (the amino acid residues from position 29 to position 201 of the amino acid sequence set forth in SEQ ID NO: 7)

A polypeptide comprising the amino acid residues from the glutamine at position 29 to the glutamine at position 201 of the amino acid sequence set forth in SEQ ID NO: 2, provided the polypeptide has a Leu190Ser amino acid substitution in the amino acid residues from position 29 to position 201.

(c) FcγRIIa-m8B (the amino acid residues from position 29 to position 201 of the amino acid sequence set forth in SEQ ID NO: 13)

A polypeptide comprising the amino acid residues from the glutamine at position 29 to the glutamine at position 201 of the amino acid sequence set forth in SEQ ID NO: 2, provided the polypeptide has the following amino acid substitutions in the amino acid residues from position 29 to position 201: Ile68Val, Gln69Leu, His80Gln, Ser84Thr, Asn90Thr, Asn91Ser, His125Arg, and Leu190Ser.

(d) FcγRIIa-m8D (the amino acid residues from position 29 to position 201 of the amino acid sequence set forth in SEQ ID NO: 17)

A polypeptide comprising the amino acid residues from the glutamine at position 29 to the glutamine at position 201 of the amino acid sequence set forth in SEQ ID NO: 2, provided the polypeptide has the following amino acid substitutions in the amino acid residues from position 29 to position 201: Ile68Val, His80Gln, Ser84Thr, Asn90Thr, Asn91Ser, Thr123Pro, His125Arg, and Leu190Ser.

(e) FcγRIIa-m10A (the amino acid residues from position 29 to position 201 of the amino acid sequence set forth in SEQ ID NO: 19)

A polypeptide comprising the amino acid residues from the glutamine at position 29 to the glutamine at position 201 of the amino acid sequence set forth in SEQ ID NO: 2, provided the polypeptide has the following amino acid substitutions in the amino acid residues from position 29 to position 201: Ile45Thr, Ile68Val, Gln69Leu, His80Gln, Ser84Thr, Asn90Thr, Asn91Ser, Thr123Pro, His125Arg, and Leu190Ser.

(f) FcγRIIa-m10C (the amino acid residues from position 29 to position 201 of the amino acid sequence set forth in SEQ ID NO: 23)

A polypeptide comprising the amino acid residues from the glutamine at position 29 to the glutamine at position 201 of the amino acid sequence set forth in SEQ ID NO: 2, provided the polypeptide has the following amino acid substitutions in the amino acid residues from position 29 to position 201: Ile68Val, Gln69Leu, His80Gln, Pro83Leu, Ser84Thr, Asn90Thr, Asn91Ser, Thr123Pro, His125Arg, and Leu190Ser.

(g) FcγRIIa-m11 (the amino acid residues from position 29 to position 201 of the amino acid sequence set forth in SEQ ID NO: 25)

A polypeptide comprising the amino acid residues from the glutamine at position 29 to the glutamine at position 201 of the amino acid sequence set forth in SEQ ID NO: 2, provided the polypeptide has the following amino acid substitutions in the amino acid residues from position 29 to position 201: Ile45Thr, Ile68Val, Gln69Leu, His80Gln, Pro83Leu, Ser84Thr, Asn90Thr, Asn91Ser, Thr123Pro, His125Arg, and Leu190Ser.

(h) FcγRIIa-m11-Del1 (the amino acid residues from position 29 to position 200 of the amino acid sequence set forth in SEQ ID NO: 35)

A polypeptide comprising the amino acid residues from the glutamine at position 29 to the glutamine at position 200 of the amino acid sequence set forth in SEQ ID NO: 2, provided the polypeptide has, in the amino acid residues from position 29 to position 200, a deletion Ser62 and the following amino acid substitutions: Ile45Thr, Ile68Val, Gln69Leu, His80Gln, Pro83Leu, Ser84Thr, Asn90Thr, Asn91Ser, Thr123Pro, His125Arg, and Leu190Ser.

(i) FcγRIIa-m11-Del5 (the amino acid residues from position 29 to position 196 of the amino acid sequence set forth in SEQ ID NO: 43)

A polypeptide comprising the amino acid residues from glutamine at position 29 to glutamine at position 196 of the amino acid sequence set forth in SEQ ID NO: 2, provided the polypeptide has, in the amino acid residues from position 29 to position 196, deletions Arg61 to Ser65 and the following amino acid substitutions: Ile45Thr, Ile68Val, Gln69Leu, His80Gln, Pro83Leu, Ser84Thr, Asn90Thr, Asn91Ser, Thr123Pro, His125Arg, and Leu190Ser.

Note that in the Fc-binding proteins set forth in SEQ ID NOs: 5, 7, 13, 17, 19, 23, and 25, the methionine at position 1 to the alanine at position 26 constitute a MalE signal peptide, the methionine at position 27 and the glycine at position 28 constitute a linker sequence, the glutamine at position 29 to the glutamine at position 201 constitute an amino acid sequence of a polypeptide (FcγRIIa-m7 (SEQ ID NO: 5), FcγRIIa-m1 (SEQ ID NO: 7), FcγRIIa-m8b (SEQ ID NO: 13), FcγRIIa-m8d (SEQ ID NO: 17), FcγRIIa-m10a (SEQ ID NO: 19), FcγRIIa-m10c (SEQ ID NO: 23) or FcγRIIa-m11 (SEQ ID NO: 25)) capable of binding to the antibody Fc region, the glycines at position 202 and position 203 constitute a linker sequence, and the histidines from position 204 to position 209 constitute a tag sequence.

Note that in the Fc-binding protein set forth in SEQ ID NO: 35, the methionine at position 1 to the alanine at position 26 constitute a MalE signal peptide, the methionine at position 27 and the glycine at position 28 constitute a linker sequence, the glutamine at position 29 to the glutamine at position 200 constitute an amino acid sequence of a polypeptide (FcγRIIa-m11-Del1) capable of binding to the antibody Fc region, the glycines at position 201 and position 202 constitute a linker sequence, and the histidines from position 203 to position 208 constitute a tag sequence.

Note that in the Fc-binding protein set forth in SEQ ID NO: 43, the methionine at position 1 to the alanine at position 26 constitute a MalE signal peptide, the methionine at position 27 and the glycine at position 28 constitute a linker sequence, the glutamine at position 29 to the glutamine at position 196 constitute an amino acid sequence of polypeptide (FcγRIIa-m11-Del5) capable of binding to the antibody Fc region, the glycines at position 197 and position 198 constitute a linker sequence, and the histidines from position 199 to position 204 constitute a tag sequence.

Examples of methods for producing a polynucleotide encoding the Fc-binding protein of the present invention (hereinafter referred to simply as the polynucleotide of the present invention) include:

(1) a method of converting the amino acid sequence of the Fc-binding protein of the present invention to a nucleotide sequence and artificially synthesizing a polynucleotide comprising the nucleotide sequence; or (2) a method of directly preparing a polynucleotide containing the whole or partial sequence of the Fc-binding protein artificially or preparing the polynucleotide from cDNA of the Fc-binding protein using a DNA amplification method such as PCR, followed by linkage of the prepared polynucleotide using a suitable method.

In the method (1) above, when converting the amino acid sequence to a nucleotide sequence, it is preferable that the conversion is performed in view of codon usage frequency of the transformed host. For example, if the host is *Escherichia coli*, the usage frequency of each of AGA/AGG/CGG/CGA for arginine (Arg), ATA for isoleucine (Ile), CTA for leucine (Leu), GGA for glycine (Gly), CCC for proline (Pro) is low (so called rare codons) and so these codons should be avoided when performing the conversion. Public databases (for example, the Codon Usage Database on the Kazusa DNA Research Institute website) can be used to perform codon usage frequency analysis.

When introducing mutations into the polynucleotide of the present invention, error prone PCR may be used. The reaction conditions for the error prone PCR are not particularly limited, provided desired mutations can be introduced into the polynucleotide encoding the human FcγRIIa (or Fc binding protein). For example, mutations can be introduced into the polynucleotide by adding the four basic types of deoxynucleotide (dATP/dTTP/dCTP/dGTP) in uneven concentrations and $MnCl_2$ at a concentration of 0.01 to 10 mM (preferably 0.1 to 1 mM) to a PCR reaction liquid and performing PCR. Methods of introducing mutations other than error prone PCR include a method of subjecting the polynucleotide containing the whole or partial sequence of human FcγRIIa to contact with or action of an agent serving as a mutagen or ultraviolet radiation to introduce and prepare mutations. The agent used as a mutagen in the above method may be any of mutagenic agents that are usually used by a person skilled in the art such as hydroxylamine, N-methyl-N'-nitro-N-nitrosoguanidine, nitrous acid, sulfurous acid, and hydrazine.

When transforming a host using the polynucleotide of the present invention, the polynucleotide of the present invention itself may be used, but it is more preferable to use an expression vector (e.g., bacteriophages, cosmids, or plasmids commonly used for transforming prokaryotic or eukaryotic cells) into which the polynucleotide of the present invention has been introduced at a suitable site. Note that there are no limitations on the expression vector, provided the expression vector is stable and can replicate within the host to be transformed. When *E. coli* is used as the host, examples of the vector include a pET plasmid vector, pUC plasmid vector, pTrc plasmid vector, pCDF plasmid vector, and pBBR plasmid vector.

Further, the "suitable site" refers to a site in the expression vector that does not destroy regions related to a replication function, preferred antibiotic marker, or transmissibility. When introducing the polynucleotide of the present invention into the expression vector, it is preferable that the polynucleotide is introduced so as to be linked to a functional polynucleotide such as a promoter necessary for expression. Examples of the promoter when the host is *E. coli* include the tip promoter, tac promoter, trc promoter, lac promoter, T7 promoter, recA promoter, Ipp promoter, in addition to λ PL promoter and λ PR promoter of λ phage.

Transformation of a host using an expression vector (hereinafter referred to as expression vector of the present invention) into which the polynucleotide of the present invention has been introduced prepared by the above method, may be performed by any method commonly used by a person skilled in the art. For example, when microorganisms belonging to the *Escherichia* genus (e.g., *E. coli* JM109, *E. coli* BL21 (DE3), and *E. coli* W3110) are selected, transformation may be carried out by any of the methods set forth in publicly available documents (e.g., Molecular Cloning, Cold Spring Harbor Laboratory, 256, 1992). Transformants obtained by the above method are screened by a suitable method, whereby transformants (hereinafter referred to as transformants of the present invention) that can express the Fc-binding protein of the present invention can be obtained. Note that there are no particular limitations on the host for expressing the Fc-binding protein of the present invention. Examples include animal cells (CHO (Chinese Hamster Ovary) cells, HEK cells, Hela cells, COS cells, etc.), yeast (*Saccharomyces cerevisiae, Pichia pastoris, Hansenula polymorpha, Schizosaccharomyces japonicus, Schizosaccharomyces octosporus, Schizosaccharomyces pombe*, etc.), insect cells (Sf9, Sf21, etc.), *Escherichia coli* (JM109, BL21(DE3), W3110, etc.) and *Bacillus subtilis*. Note that using animal cells or *E. coli* as the host is preferable in terms of productivity and using *E. coli* as the host is more preferable.

For the preparation of the expression vector of the present invention from the transformant of the present invention, the expression vector may be prepared using the alkali extraction method or a commercially available extraction kit such as QIAprep Spin Miniprep kit (QIAGEN N.V.) from a culture product obtained by culturing the transformant of the present invention. The Fc binding protein of the present invention can be prepared by culturing the transformant of the present invention and harvesting the Fc binding protein of the present invention from the obtained culture product. Note that herein, the culture product also includes the culture medium used for culturing in addition to the cultured transformed cells of the present invention themselves. The transformant used in the protein production method of the present invention may be cultured in a culture medium appropriate for the designated host, and when the host is *E. coli*, an example of a preferred culture medium is LB (Luria-Bertani) culture medium supplemented with a necessary nutritional source. Note that in order to selectively grow the transformant of the present invention due to the presence or absence of introduction of the vector of the present invention, it is preferable to perform culturing in a culture medium having added thereto an antibiotic which corresponds to an antibiotic resistance gene contained in the vector. For example, if the vector contains a kanamycin resistance gene, kanamycin may be added to the culture medium. Further, in addition to sources of carbon, nitrogen, and inorganic salts, suitable nutritional sources may be added including one or more reducing agents selected from the group consisting of glutathione, cysteine, cystamine, thioglycolate and dithiothreitol as desired. Furthermore, a reagent such as glycine that promotes the secretion of proteins from the transformant into the culture medium may be added, specifically, if the host is *E. coli*, it is preferable for not more than 2% (w/v) of glycine to be added to the culture medium. If the host is *E. coli*, the culture temperature is generally 10° C. to 40° C., preferably 20° C. to 37° C., more preferably about 25° C. but can be selected according to the characteristics of the expressed protein. If the host is *E. coli*, the pH of the culture medium is set to pH 6.8 to pH 7.4 and preferably around pH 7.0. Further, if the vector of the present invention contains an inducible promoter, it is preferable that the promoter is induced under conditions which favor the expression of the Fc-binding protein of the present invention. An example of an inducing agent is IPTG (isopropyl-β-D-thiogalactopyranoside). If the host is *E. coli*, expression of the Fc-binding protein can be induced by measuring the turbidity of the culture solution (absorbance at 600 nm), adding a suitable amount of IPTG when the turbidity is around 0.5 to 1.0, and then continuing culturing. The concentration of the IPTG added may be appropriately selected from a range of 0.005 to 1.0 mM but is preferably in a range of 0.01 to 0.5 mM. Various conditions related to IPTG induction may be selected from well-known conditions in this technical field.

In order to harvest the Fc-binding protein of the present invention from a culture product obtained by culturing the transformant of the present invention, a method suited to the expression form of the Fc-binding protein of the present invention in the transformant of the present invention may be used to separate/purify the Fc-binding protein of the present invention from the culture product to harvest the Fc-binding protein. For example, if the Fc-binding protein is expressed in the supernatant of the culture medium, centrifugation may be performed to separate the protein from the bacterial cells and the Fc-binding protein of the present invention may be purified from the obtained culture supernatant. Further, if the Fc-binding protein is expressed intracellularly (including the periplasm), the bacterial cells can be collected by centrifugation, the cells can be disrupted by the addition of an enzyme treatment agent or a surfactant and the Fc-binding protein of the present invention can be extracted and then purified. In order to purify the Fc-binding protein of the present invention, publicly known methods in the technical field, for example, separation/purification using liquid chromatography may be used. Liquid chromatography includes ion exchange chromatography, hydrophobic interaction chromatography, gel filtration chromatography, and affinity chromatography, and by combining such chromatographic methods when carrying out purification, the Fc-binding protein of the present invention can be prepared to a high degree of purity. Methods for measuring the binding activity of the obtained Fc-binding protein of the present invention to IgG include, for example, measurements of the binding activity to IgG using an enzyme-linked immunosorbent assay (hereinafter referred to as ELISA) or surface plasmon resonance. For the IgG used for measuring binding activity, human IgG is preferable, and any of human IgG1, human IgG2, human IgG3, or human IgG4 may be used.

The adsorbent of the present invention can be prepared by binding the Fc-binding protein of the present invention to an insoluble carrier. There are no particular limitations on the insoluble carrier which may include, for example: carriers made from polysaccharides, such as agarose, alginate (alginic acid salt), carrageenan, chitin, cellulose, dextrin, dextran, and starch; carriers made from synthetic polymers, such as polyvinyl alcohol, polymethacrylate, poly(2-hydroxyethylmethacrylate), and polyurethane; and carriers made from ceramics such as silica. Thereamong, carriers made from polysaccharides or synthetic polymers are preferable as the insoluble carrier. Examples of the preferable carrier include hydroxylated polymethacrylate gels such as Toyopearl (manufactured by Tosoh Corporation), agarose gels such as Sepharose (manufactured by GE Healthcare), and cellulose gels such as Cellufine (manufactured by JNC). There are no limitations to the form of the insoluble carrier which may be granular, non-granular, porous, or non-porous.

In order to immobilize the Fc-binding protein onto the insoluble carrier, an activating group such as an N-hydroxysuccinimide (NHS) activated ester group, an epoxy group, a carboxyl group, a maleimide group, a haloacetyl group, a tresyl group, a formyl group, or a haloacetamide is provided on the insoluble carrier and immobilization may be achieved by covalent bonding between the Fc-binding protein and the insoluble carrier via the activating group. Commercially available carriers provided with an activating group may be used as they are or may be prepared by introducing an activating group to the surface of a carrier under appropriate reaction conditions. Examples of commercially available carriers provided with an activating group include TOYOPEARL AF-Epoxy-650M, TOYOPEARL AF-Tresyl-650M (both manufactured by Tosoh Corp.), HiTrap NHS-activated HP Columns, NHS-activated Sepharose 4Fast, Flow, Epoxy-activated Sepharose 6B (both manufactured by GE Healthcare), SulfoLink Coupling Resin (manufactured by Thermo Scientific).

Meanwhile, examples of a method for introducing an activating group onto the carrier surface include a method of reacting a hydroxy group, epoxy group, carboxyl group, or amino group on the surface of the carrier with one of at least two active sites of a compound. Examples thereof include compounds that introduce an epoxy group to a hydroxy group or amino group of the carrier surface, and examples of the compounds include epichlorohydrin, ethanediol diglycidyl ether, butanediol diglycidyl ether, and hexanediol diglycidyl ether. Examples of compounds that introduce carboxyl groups to the carrier surface after the above compound has introduced an epoxy group to the carrier surface include 2-mercaptoacetic acid, 3-mercaptopropionic acid, 4-mercaptobutyric acid, 6-mercaptobutyric acid, glycine, 3-aminopropionic acid, 4-aminobutyric acid, and 6-aminohexanoic acid.

Examples of a compound that introduces a maleimide group onto a hydroxyl group, an epoxy group, a carboxyl group, or an amino group existing on the surface of a carrier include N-(ε-maleimidocaproic acid) hydrazide, N-(ε-maleimidopropionic acid) hydrazide, 4-(4-N-maleimidophenyl) acetic acid hydrazide, 2-aminomaleimide, 3-aminomaleimide, 4-aminomaleimide, 6-aminomaleimide, 1-(4-aminophenyl)maleimide, 1-(3-aminophenyl)maleimide, 4-(maleimido)phenylisocyanate, 2-maleimidoacetic acid, 3-maleimidopropionic acid, 4-maleimidobutyric acid, 6-maleimidohexanoic acid, N-(α-maleimidoacetoxy)succinimide ester, (m-maleimidobenzoyl) N-hydroxysuccinimide ester, succinimidyl-4-(maleimidomethyl)cyclohexane-1-carbonyl-6-aminohexanoic acid, succinimidyl-4-(maleimidomethyl)cyclohexane-1-carboxylic acid, (p-maleimidobenzoyl) N-hydroxysuccinimide ester, (m-maleimidobenzoyl) N-hydroxysuccinimide ester.

Examples of a compound that introduces a haloacetyl group onto a hydroxyl group or an amino group existing on the surface of the carrier include chloroacetic acid, bromoacetic acid, iodoacetic acid, chloroacetic acid chloride, bromoacetic acid chloride, bromoacetic acid bromide, chloroacetic acid anhydride, bromoacetic acid anhydride, iodoacetic anhydride, 2-(iodoacetamido)acetic acid-N-hydroxysuccinimide ester, 3-(bromoacetamido)propionic acid-N-hydroxysuccinimide ester, 4-(iodoacetyl)aminobenzoic acid-N-hydroxysuccinimide ester. Note that the examples further include a method of reacting hydroxyl groups and amino groups existing on the surface of the carrier with w-alkenyl alkane glycidyl ether then activating the w-alkenyl moiety by halogenation with a halogenating agent. Examples of the w-alkenyl alkane glycidyl ether include allyl glycidyl ether, 3-butenyl glycidyl ether and 4-pentenyl glycidyl ether, and examples of halogenating agents include N-chlorosuccinimide, N-bromosuccinimide and N-iodosuccinimide.

Another example of a method for introducing an activating group onto the carrier surface includes a method of introducing an activating group to a carboxyl group existing on the surface of the carrier by using a condensing agent and an additive. Examples of the condensing agent include 1-ethyl-3-(3-dimethylaminopropyl) carbodiimide (EDC), dicyclohexyl carbodiamide and carbonyldiimidazole. Further, examples of additives include N-hydroxysuccinimide (NHS), 4-nitrophenol and 1-hydroxybenzotriazole.

Examples of a buffer solution used when immobilizing the Fc-binding protein of the present invention on an insoluble carrier include acetate buffer, phosphate buffer, MES (2-morpholinoethane sulfonic acid) buffer, HEPES (2-[4-(2-Hydroxyethyl)-1-piperazinyl]ethansulfonic acid buffer, Tris buffer, and borate buffer. The reaction temperature during immobilization is suitably set within the temperature range of 5° C. to 50° C. in view of the reactivity of the activating group and stability of the Fc-binding protein of the present invention, and is preferably within the range of 10° C. to 35° C.

In order to purify an antibody using the adsorbent of the present invention obtained by immobilizing the Fc-binding protein of the present invention on the insoluble carrier, for example, a buffer solution containing the antibody is added to a column packed with the adsorbent of the present invention using a pump or other means to transfer liquid, whereby the antibody specifically binds to the adsorbent of the present invention, and thereafter the antibody can be eluted from the column by adding a suitable eluting agent. Note that antibody that can be purified by the adsorbent of the present invention is an antibody that includes at least an Fc region having affinity for the Fc-binding protein. Examples of the antibody used in antibody drugs include commonly used chimeric antibodies, humanized antibodies, human antibodies and amino acid substitution products thereof. Further, antibodies that have artificially been structurally modified, such as bispecific antibodies, fusion antibodies consisting of an antibody Fc region and another protein, or conjugates consisting of an antibody Fc region and a drug (antibody-drug conjugates, ADC) can also be purified with the adsorbent of the present invention. Furthermore, prior to adding the buffer containing the antibody into the column, by equilibrating the column using a suitable buffer solution, the antibodies can be purified to a higher degree of purity, which is preferable. Examples of the buffer solution include a phosphate buffer and other buffer solutions containing an inorganic salt as a component thereof. The pH thereof is pH 3.0 to 10.0, preferably pH 5.0 to 8.0.

In order to elute the antibody adsorbed to the adsorbent of the present invention, interactions between the antibody and the ligand (Fc-binding protein of the present invention) can be weakened. Specific examples thereof include changing pH with a buffer solution, using a counter peptide, changing the temperature, and changing the salt concentration. Specific examples of eluents for eluting antibodies adsorbed to the adsorbent include buffer solutions that are more acidic than the solution used when adsorbing antibodies to the adsorbent of the present invention. Examples of this type of buffer solution include a citrate buffer solution, glycine-hydrochloric acid buffer solution and acetate buffer solution capable of buffering in the acidic range. The pH of the buffer solution may be set within a range that does not impair the antibody function and is preferably pH 2.5 to 6.0, more preferably pH 3.0 to 5.0, and even more preferably pH 3.3 to 4.0.

Advantageous Effects of Invention

The Fc-binding protein of the present invention is a protein wherein an amino acid residue at a specific site in the extracellular region of wild type human FcγRIIa has been substituted with another amino acid or deleted. The Fc-binding protein of the present invention has improved acid stability compared to wildtype human FcγRIIa. Accordingly, the Fc-binding protein of the present invention is useful as a ligand of an adsorbent for separating antibodies (immunoglobulins).

EXAMPLES

Figure 1:
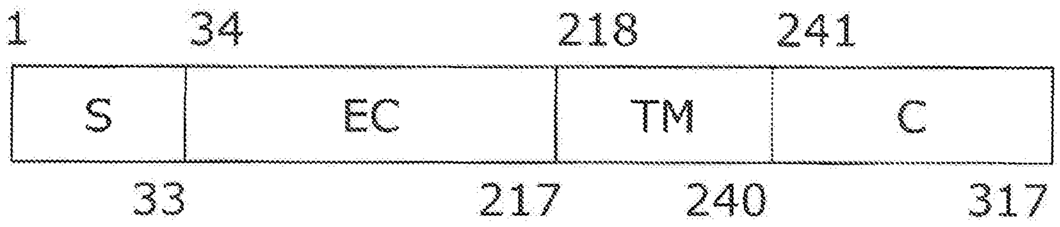
FIG. 1 is a schematic diagram of the FcγRIIa. The numbers in the drawing indicate the positions in the amino acid sequence of SEQ ID NO: 1. In the drawing, S represents a signal sequence, EC represents an extracellular region, TM represents a transmembrane region and C represents an intercellular region.

The following examples are provided to describe the present invention in more detail but the present invention is not limited thereby.

Example 1 Introduction of Mutations into Fc-Binding Protein and Construction of Library In an expression vector pET-Am6 for expressing the Fc-binding protein consisting of the amino acid sequence set forth in SEQ ID NO: 3, random mutations were introduced into the section of the polynucleotide (SEQ ID NO: 4) encoding the Fc-binding protein by error prone PCR. Note that the Fc-binding protein consisting of the sequence set forth in SEQ ID NO: 3 was obtained by introducing amino acid substitutions at the six sites indicated below into an Fc-binding protein consisting of the sequence set forth in SEQ ID NO: 2 and comprising the wildtype human FcγRIIa extracellular domain.

Substitution of isoleucine to valine at position 68 of SEQ ID NO: 2 (position 73 in SEQ ID NO: 1).

Substitution of histidine to glutamine at position 80 of SEQ ID NO: 2 (position 85 in SEQ ID NO: 1).

Substitution of serine to threonine at position 84 of SEQ ID NO: 2 (position 89 in SEQ ID NO: 1).

Substitution of asparagine to threonine at position 90 of SEQ ID NO: 2 (position 95 in SEQ ID NO: 1).

Substitution of asparagine to serine at position 91 of SEQ ID NO: 2 (position 96 in SEQ ID NO: 1).

Substitution of histidine to arginine at position 125 of SEQ ID NO: 2 (position 130 in SEQ ID NO: 1).

(1) Error prone PCR was performed using the above pET-Am6 as template DNA. Error prone PCR was performed as follows using the primers set forth in SEQ ID NOs: 8 and 9. A reaction solution having the composition shown in Table 1 was prepared and then subjected to heat treatment for 2 minutes at 95° C., the reaction solution was then subjected to 35 reaction cycles each involving a first step at 95° C. for 30 seconds, a second step at 60° C. for 30 seconds, and a third step at 72° C. for 90 seconds, before finally undergoing heat treatment for 7 minutes at 72° C.

TABLE 1

| COMPOSITION | VOLUME |
|---|---|
| Template DNA (10 ng/μL) | 1 μL |
| 10 mM $MnCl_2$ | 4 μL |
| 10 mM dATP | 2 μL |
| 10 mM dGTP | 2 μL |
| 10 mM dCTP | 12 μL |
| 10 mM dTTP | 8 μL |
| Primer(SEQ ID NO: 8, 10 pmol/μL) | 4 μL |
| Primer(SEQ ID NO: 9, 10 pmol/μL) | 4 μL |
| 10 × Ex Taq Buffer | 10 μL |
| 25 mM $MgCl_2$ | 12 μL |
| GoTaq polymerase(Promega Corporation) | 1 μL |
| $H_2O$ | up to 100 μL |

(2) The PCR product obtained in (1) was purified, digested with the restriction enzymes NcoI and HindIII, and then ligated into the expression vector pETMalE (Japanese Unexamined Patent Publication (Kokai) No. 2011-206046) which had been digested with the same restriction enzymes beforehand.

(3) Following completion of the ligation reaction, the reaction solution was introduced into *E. coli* BL21 (DE3) by the heat shock method, the *E. coli* were then cultured on LB plate medium containing 50 μg/mL of kanamycin (for 18 hours at 37° C.) and the colonies that formed on the plate were used as a random mutant library.

Example 2 Screening of Acid Resistant Fc-Binding Protein (1) The random mutant library produced in EXAMPLE 1 (transformants) was inoculated into 200 μL of a 2YT liquid culture medium (peptone: 16 g/L, yeast extract: 10 g/L, sodium chloride: 5 g/L) containing 50 μg/mL of kanamycin, and then shake cultured overnight at 30° C. using a 96-well deep well plate.

(2) After culturing, 5 μL of the culture solution was subcultured in 500 μL of a 2YT liquid culture medium containing 0.05 mM of IPTG (isopropyl-β-D-thiogalactopyranoside), 0.3% (w/v) glycine and 50 μg/mL of kanamycin, followed by additional shake culturing overnight at 20° C. using a 96-well deep well plate.

(3) After culturing, 20 μL of a culture supernatant containing each Fc-binding protein obtained by centrifugation was mixed with 80 μL of 0.1 M glycine hydrochloride buffer (pH 3.0), and left standing for 24 hours at 25° C.

(4) The antibody binding activity of the Fc-binding protein when subjected to acid treatment of (3) and the antibody binding activity of the Fc-binding protein when not subjected to acid treatment of (3) were each measured according to the ELISA procedure indicated below and residual activity was calculated by dividing the antibody binding activity when the Fc-binding protein was subjected to acid treatment by the antibody binding activity when the Fc-binding protein was not subjected to acid treatment.

(4-1) A preparation of gamma-globulin (The Chemo-Sero-Therapeutic Research Institute), which is a human antibody, was immobilized in wells of a 96-well microplate at 1 μg/well (for 18 hours at 4° C.). Following completion of immobilization, the reaction was blocked with 20 mM Tris-hydrochloric acid buffer (pH 7.4) containing 2% (w/v) skim milk (manufactured by BD) and 150 mM sodium chloride.

(4-2) The microplate was washed with a washing buffer (20 mM Tris-HCl buffer (pH 7.4) containing 0.05% (w/v) Tween 20 and 150 mM NaCl). Then a solution containing the Fc-binding protein to be evaluated for antibody binding activity was added and the Fc-binding protein was allowed to react with the immobilized gamma-globulin (for 1 hour at 30° C.).

(4-3) Following completion of the reaction, the microplate was washed with the above washing buffer and then an Anti-6His antibody (manufactured by Bethyl Laboratories) diluted to 100 ng/mL was added at 100 μL/well.

(4-4) The reaction was performed for 1 hour at 30° C. and washed with the above washing buffer and then TMB Peroxidase Substrate (manufactured by KPL) was added at 50 μL/well. Coloring was interrupted by adding 1 M phosphoric acid at 50 μL/well, and optical absorbance at 450 nm was measured with a microplate reader (Tecan Trading).

(5) Approximately 700 strains of transformants were evaluated using the method of (4), and therefrom, transformants that expressed Fc-binding protein having improved acid stability compared to the Fc-binding protein consisting of the amino acid sequence set forth in SEQ ID NO: 3 were selected. The selected transformants were then cultured and expression vectors were prepared using the QIAprep Spin Miniprep Kit (Qiagen).

(6) The sequence of the polynucleotide region encoding the Fc-binding protein inserted into the obtained expression vector was subjected to a cycle sequence reaction using the Big Dye Terminator Cycle Sequencing FS Read Reaction Kit (PE Applied Biosystems) based on the chain termination method, followed by analysis of the nucleotide sequence thereof with a fully-automated DNA sequencer-ABI Prism 3700 DNA Analyzer (PE Applied Biosystems) and the sites of the amino acid mutations were identified. Note that during this analysis, an oligonucleotide consisting of the sequence set forth in either SEQ ID NO: 8 or 9 was used as the sequence primer.

Figure 2:
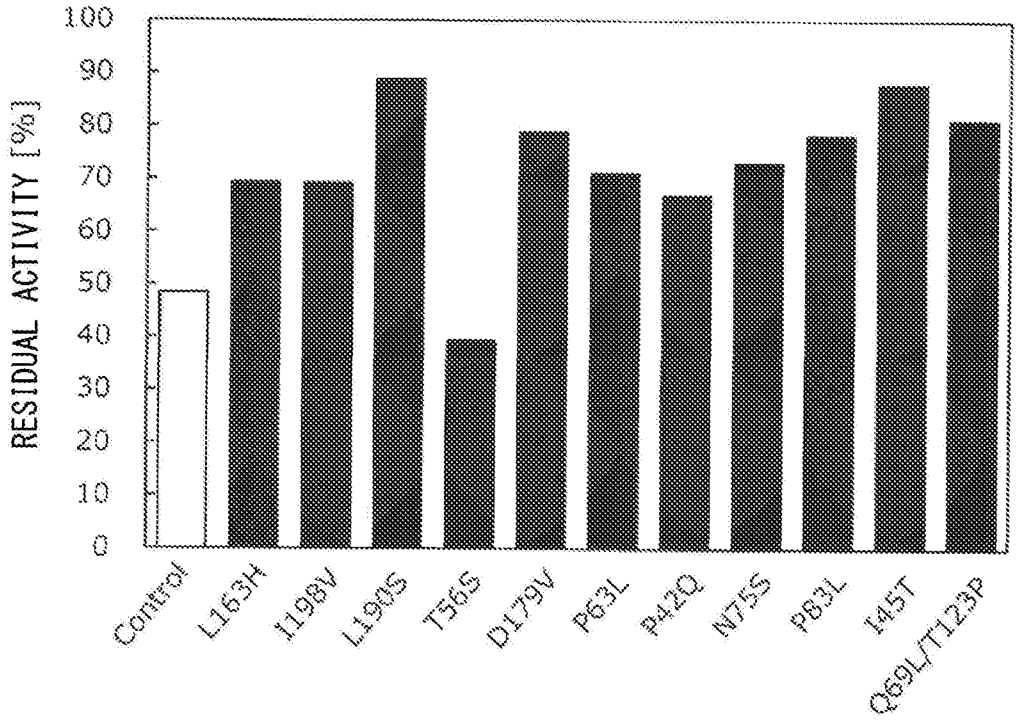
FIG. 2 is a graph indicating the results of evaluation of acid resistivity of Fc binding proteins in which an amino acid at one site or amino acids at two sites have been substituted as compared to the Fc binding protein consisting of the amino acid sequence set forth in SEQ ID NO: 3 (control).

The positions of amino acid substitutions and the residual activities (%) after acid treatment of Fc-binding proteins expressed by transformants selected in (5) with respect to the Fc-binding protein (control) consisting of the amino acid sequence set forth in SEQ ID NO: 3 are summarized in FIG. 2. Compared to the control, Fc-binding proteins which have undergone the following substitutions were found to have improved acid stability: Pro42Gln (this represents a substitution of proline to glutamine at position 42 of SEQ ID NO: 2 (position 47 in SEQ ID NO: 1), this also applies to the following), Pro63Leu, Asn75Ser, Leu163His, Asp179Val, Leu190Ser, Ile198Val, Ile45Thr, Gln69Leu, Pro83Leu, or Thr123Pro. Accordingly, including at least one of the amino acid substitutions at the 11 sites in the extracellular domain of human FcγRIIa was found to improve acid stability (acid resistance). Since residual activity was the highest for Leu190Ser thereamong, it was found that Fc-binding proteins having at least the Leu190Ser amino acid substitution in the extracellular domain of human FcγRIIa have particularly improved acid stability (acid resistance).

Among the Fc-binding proteins with improved acid stability obtained in the present example, the amino acid sequence of the Fc-binding protein having the Leu190Ser amino acid substitution is set forth in SEQ ID NO: 5 and the sequence of a polynucleotide encoding the protein is set forth in SEQ 1D NO: 6. Note that in SEQ ID NO: 5, the methionine (Met) at position 1 to the alanine (Ala) at position 26 constitute a MalE signal peptide, the methionine (Met) at position 27 and the glycine (Gly) at position 28 constitute a linker sequence, the glutamine (Gln) at position 29 to the glutamine (Gln) at position 201 constitute a polypeptide capable of binding to the Fc region (FcγRIIa-m7), the glycines (Gly) at position 202 and position 203 constitute a linker sequence, and the histidines from position 204 to position 209 constitute a tag sequence. Further, FcγRIIa-m7 is a polypeptide comprising amino acid residues from the glutamine at position 29 to the glutamine at position 201 of the amino acid sequence set forth in SEQ ID NO: 2, and having the following amino acid substitutions in the amino acid residues from position 29 to position 201: Ile68Val, His80Gln, Ser84Thr, Asn90Thr, Asn91Ser, His125Arg, and Leu190Ser.

Example 3 Introduction of Further Amino Acid Substitutions (1)

The amino acid substitutions involved in improving the acid stability of the Fc-binding protein found in EXAMPLE 2 were further introduced into FcγRIIa-m7 to further improve the acid stability. Introduction (accumulation) of amino acid substitutions was mainly carried out using PCR, and the four types of polypeptides shown in (a) to (d) below were prepared.

(a) a polypeptide (named FcγRIIa-m8A) wherein an Ile45Thr amino acid substitution was further introduced to FcγRIIa-m7, (b) a polypeptide (named FcγRIIa-m8B) wherein a Gln69Leu amino acid substitution was further introduced to FcγRIIa-m7, (c) a polypeptide (named FcγRIIa-m8C) wherein a Pro83Leu amino acid substitution was further introduced to FcγRIIa-m7, (d) a polypeptide (named FcγRIIa-m8D) wherein a Thr123Pro amino acid substitution was further introduced to FcγRIIa-m7.

The method of preparing each Fc-binding protein is described in detail below.

(a) FcγRIIa-m8A

Ile45Thr was selected from among the amino acid substitutions contributing to acid stability elucidated in EXAMPLE 2 and was accumulated in FcγRIIa-m8 to prepare FcγRIIa-m8A. Specifically, a mutation causing Ile45Thr was introduced to the polynucleotide encoding FcγRIIa-m7 obtained in EXAMPLE 2 to prepare FcγRIIa-m8A.

(a-1) The polynucleotide (SEQ 1D NO: 6) encoding the Fc-binding protein comprising FcγRIIa-m7 obtained in EXAMPLE 2 was used as a template and PCR was performed thereon using oligonucleotides consisting of the sequences set forth in SEQ 1D NO: 8 and SEQ ID NO: 27 as PCR primers. PCR was carried out by preparing a reaction solution having the composition shown in Table 2 and then subjecting the solution to heat treatment for 5 minutes at 98° C., followed by 30 reaction cycles each involving a first step at 98° C. for 10 seconds, a second step at 55° C. for 5 seconds, and a third step at 72° C. for 1 minute, before finally undergoing heat treatment for 5 minutes at 72° C. The amplified PCR product was subjected to agarose gel electrophoresis and purified from the gel using QIAquick Gel Extraction Kit (manufactured by Qiagen). The purified PCR product was named m8A-F.

TABLE 2

| COMPOSITION | VOLUME |
|---|---|
| Template DNA | 2 μL |
| 2.5 mM dNTPs | 2 μL |
| 10 μM Forward primer | 1 μL |
| 10 μM Reverse primer | 1 μL |
| 5 × PrimeSTAR Buffer(TAKARA BIO INC.) | 4 μL |
| 2.5 U/mL PrimeSTAR HS(TAKARA BIO INC.) | 0.5 μL |
| $H_2O$ | up to 20 μL |

(a-2) Using the same polynucleotide as in (a-1) as a template, PCR and PCR product purification were performed using the same methods as in (a-1) other than using oligonucleotides consisting of the sequences set forth in SEQ ID NO: 26 and SEQ ID NO: 9 as PCR primers. The purified PCR product was named m8A-S.

(a-3) The two types of PCR product obtained in (a-1) and (a-2) (m8A-F and m8A-S) were mixed and a reaction solution comprising the components shown in Table 3 was prepared. PCR was carried out by subjecting the reaction solution to heat treatment for 5 minutes at 98° C., followed by 5 reaction cycles each involving a first step at 98° C. for 10 seconds, a second step at 55° C. for 5 seconds, and a third step at 72° C. for 1 minute and a PCR product m8A-FL in which the m8A-F and 8A-S were linked was obtained.

TABLE 3

| COMPOSITION | VOLUME |
|---|---|
| PCR product | 1 μL |
| 2.5 mM dNTPs | 2 μL |
| 5 × PrimeSTAR | 4 μL |

TABLE 3-continued

| COMPOSITION | VOLUME |
|---|---|
| Buffer(TAKARA BIO INC.) | |
| 2.5 U/mL PrimeSTAR HS(TAKARA BIO INC.) | 0.5 μL |
| $H_2O$ | up to 20 μL |

(a-4) The PCR product m8A-FL obtained in (a-3) was used as a template, and PCR was performed using oligonucleotides consisting of the sequences set forth in SEQ ID NO: 8 and SEQ ID NO: 9 as PCR primers. PCR was carried out by preparing a reaction solution having the composition shown in Table 4 and then subjecting the solution to heat treatment for 5 minutes at 98° C., followed by 30 reaction cycles each involving a first step at 98° C. for 10 seconds, a second step at 55° C. for 5 seconds, and a third step at 72° C. for 1 minute. Thereby a polynucleotide encoding FcγRIIa-m8A was prepared.

TABLE 4

| COMPOSITION | VOLUME |
|---|---|
| PCR product | 2 μL |
| 2.5 mM dNTPs | 4 μL |
| 10 μM Forward primer | 2 μL |
| 10 μM Reverse primer | 2 μL |
| 5 × PrimeSTAR Buffer(TAKARA BIO INC.) | 10 μL |
| 2.5 U/mL PrimeSTAR HS(TAKARA BIO INC.) | 1 μL |
| $H_2O$ | up to 50 μL |

(a-5) The polynucleotide obtained in (a-4) was purified, digested with the restriction enzymes NcoI and HindIII, and then ligated into the expression vector pETMalE (Japanese Unexamined Patent Publication (Kokai) No. 2011-206046) which had been digested with the restriction enzymes NcoI and HindIII beforehand. This was used to transform *E. coli* BL21 (DE3).

(a-6) The obtained transformants were cultured in LB culture medium to which 50 μg/mL of kanamycin had been added. By extracting plasmids from the harvested bacteria (transformants) the plasmid pET-m8A containing a polynucleotide encoding FcγRIIa-m8A which is a polynucleotide with an additional amino acid substitution at one site with respect to FcγRIIa-m7 was obtained.

(a-7) Sequence analysis of the nucleotide sequence of pET-m8 was performed using the same method as in EXAMPLE 2 (6).

The amino acid sequence of the FcγRIIa-m8a to which a signal sequence and a polyhistidine tag have been added is set forth in SEQ ID NO: 11 and the sequence of a polynucleotide encoding this FcγRIIa-m8a is set forth in SEQ ID NO: 10. Note that in SEQ ID NO: 11, the methionine (Met) at position 1 to the alanine (Ala) at position 26 constitute a MalE signal peptide, the methionine (Met) at position 27 and the glycine (Gly) at position 28 constitute a linker sequence, the glutamine (Gln) at position 29 to the glutamine (Gln) at position 201 constitute the FcγRIIa-m8A amino acid sequence (corresponding to the region of SEQ ID NO: 1 from position 34 to position 206), the glycines (Gly) at position 202 and position 203 constitute a linker sequence, and the histidines (His) from position 204 to position 209 constitute a tag sequence.

(b) FcγRIIa-m8B

Gln69Leu was selected from among the amino acid substitutions contributing to improved acid stability elucidated in EXAMPLE 2 and was accumulated in FcγRIIa-m7 to prepare FcγRIIa-m8B. Specifically, a mutation causing Gln69Leu was introduced to the polynucleotide encoding FcγRIIa-m7 obtained in EXAMPLE 2 to prepare FcγRIIa-m8B.

(b-1) The polynucleotide (SEQ ID NO: 6) encoding the Fc-binding protein comprising FcγRIIa-m7 obtained in EXAMPLE 2 was used as a template, and PCR and PCR product purification were performed using the same methods as in (a-1) other than using oligonucleotides consisting of the sequences set forth in SEQ ID NO: 8 and SEQ ID NO: 29 as PCR primers. The purified PCR product was named m8B-F.

(b-2) Using the same polynucleotide as in (b-1) as a template, PCR and PCR product purification were performed using the same methods as in (a-1) other than using oligonucleotides consisting of the sequences set forth in SEQ ID NO: 28 and SEQ ID NO: 9 as PCR primers. The purified PCR product was named m8B-S.

(b-3) PCR was performed using the same method as in (a-3) other than using m8B-F obtained in (b-1) and m8B-S obtained in (b-2) as PCR products, and a PCR product m8B-FL having m8B-F and m8B-S linked together was obtained.

(b-4) The PCR product m8B-FL obtained in (b-3) was used as a template, and PCR was performed using the same method as in (a-4) other than using oligonucleotides consisting of the sequences set forth in SEQ ID NO: 8 and SEQ ID NO: 9 as PCR primers. Thereby, a polynucleotide encoding FcγRIIa-m8B was prepared.

(b-5) The polynucleotide obtained in (b-4) was purified, digested with the restriction enzymes NcoI and HindIII, and then ligated into the expression vector pETMalE (Japanese Unexamined Patent Publication (Kokai) No. 2011-206046) which had been digested with restriction enzymes NcoI and HindIII beforehand. This was used to transform *E. coli* BL21 (DE3).

(b-6) The obtained transformants were cultured in LB culture medium to which 50 μg/mL of kanamycin had been added. By extracting plasmids from the harvested bacteria (transformants) the plasmid pET-FcγRIIa-m8B containing a polynucleotide encoding FcγRIIa-m8B which is a polynucleotide with an additional amino acid substitution at one site with respect to FcγRIIa-m7 was obtained.

(b-7) Sequence analysis of the nucleotide sequence of pET-FcγRIIa-m8 was performed using the same method as in EXAMPLE 2 (6).

The amino acid sequence of the FcγRIIa-m8B to which a signal sequence and a polyhistidine tag have been added is set forth in SEQ ID NO: 13 and the polynucleotide sequence encoding this FcγRIIa-m8a is set forth in SEQ ID NO: 12. Note that in SEQ ID NO: 13, the methionine (Met) at position 1 to the alanine (Ala) at position 26 constitute a MalE signal peptide, the methionine (Met) at position 27 and the glycine (Gly) at position 28 constitute a linker sequence, the glutamine (Gln) at position 29 to the glutamine (Gln) at position 201 constitute the FcγRIIa-m8B amino acid sequence (corresponding to the region of SEQ ID NO: 1 from position 34 to position 206), the glycines (Gly) at position 202 and position 203 constitute a linker sequence, and the histidines (His) from position 204 to position 209 constitute a tag sequence.

(c) FcγRIIa-m8C

Pro83Leu was selected from among the amino acid substitutions contributing to improved acid stability elucidated in EXAMPLE 2 and was accumulated in FcγRIIa-m7 to prepare FcγRIIa-m8C. Specifically, a mutation causing Pro83Leu was introduced to the polynucleotide encoding FcγRIIa-m7 obtained in EXAMPLE 2 to prepare FcγRIIa-m8C.

(c-1) The polynucleotide (SEQ ID NO: 6) encoding the Fc-binding protein comprising FcγRIIa-m7 obtained in EXAMPLE 2 was used as a template, and PCR and PCR product purification were performed using the same methods as in (a-1) other than using oligonucleotides consisting of the sequences set forth in SEQ ID NO: 8 and SEQ ID NO: 31 as PCR primers. The purified PCR product was named m8C-F.

(c-2) Using the same polynucleotide as in (c-1) as a template, PCR and PCR product purification was performed using the same method as in (a-1) other than using oligonucleotides consisting of the sequences set forth in SEQ ID NO: 30 and SEQ ID NO: 9 as PCR primers. The purified PCR product was named m8C-S.

(c-3) PCR was performed using the same method as in (a-3) other than using m8C-F obtained in (c-1) and m8C-S obtained in (c-2) as PCR products, and a PCR product m8C-FL having m8C-F and m8C-S linked together was obtained.

(c-4) The PCR product m8C-FL obtained in (c-3) was used as a template, and PCR was performed using the same method as in (a-4) other than using oligonucleotides consisting of the sequences set forth in SEQ ID NO: 8 and SEQ ID NO: 9 as PCR primers. Thereby, a polynucleotide encoding FcγRIIa-m8C was prepared.

(c-5) The polynucleotide obtained in (c-4) was purified, digested with the restriction enzymes NcoI and HindIII, and then ligated into the expression vector pETMalE (Japanese Unexamined Patent Publication (Kokai) No. 2011-206046) which had been digested with the restriction enzymes NcoI and HindIII beforehand. This was used to transform *E. coli* BL21 (DE3).

(c-6) The obtained transformants were cultured in LB culture medium to which 50 μg/mL of kanamycin had been added. By extracting plasmids from the harvested bacteria (transformants) the plasmid pET-FcγRIIa-m8C containing a polynucleotide encoding FcγRIIa-m8C which is a polynucleotide with an additional amino acid substitution at one site with respect to FcγRIIa-m7 was obtained.

(c-7) Sequence analysis of the nucleotide sequence of pET-FcγRIIa-m8C was performed using the same method as in EXAMPLE 2 (6).

The amino acid sequence of the FcγRIIa-m8C to which a signal sequence and a polyhistidine tag have been added is set forth in SEQ ID NO: 15 and the polynucleotide sequence encoding this FcγRIIa-m8C is set forth in SEQ ID NO: 14. Note that in SEQ ID NO: 15, the methionine (Met) at position 1 to the alanine (Ala) at position 26 constitute a MalE signal peptide, the methionine (Met) at position 27 and the glycine (Gly) at position 28 constitute a linker sequence, the glutamine (Gln) at position 29 to the glutamine (Gln) at position 201 constitute the FcγRIIa-m8C amino acid sequence (corresponding to the region of SEQ ID NO: 1 from position 34 to position 206), the glycines (Gly) at position 202 and position 203 constitute a linker sequence, and the histidines (His) from position 204 to position 209 constitute a tag sequence.

(d) FcγRIIa-m8D

Thr123Pro was selected from among the amino acid substitutions contributing to improved acid stability elucidated in EXAMPLE 2 and was accumulated in FcγRIIa-m7 to prepare FcγRIIa-m8D. Specifically, a mutation causing Thr123Pro was introduced to the polynucleotide encoding FcγRIIa-m7 obtained in EXAMPLE 2 to prepare FcγRIIa-m8D.

(d-1) The polynucleotide (SEQ ID NO: 6) encoding the Fc-binding protein comprising FcγRIIa-m7 obtained in EXAMPLE 2 was used as a template, and PCR and PCR product purification were performed using the same methods as in (a-1) other than using oligonucleotides consisting of the sequences set forth in SEQ ID NO: 8 and SEQ ID NO: 33 as PCR primers. The purified PCR product was named m8D-F.

(d-2) Using the same polynucleotides as in (d-1) as a template, PCR and PCR product purification were performed using the same methods as in (a-1) other than using oligonucleotides consisting of the sequences set forth in SEQ ID NO: 32 and SEQ ID NO: 9 as PCR primers. The purified PCR product was named m8D-S.

(d-3) PCR was performed using the same method as in (a-3) other than using m8C-F obtained in (d-1) and m8C-S obtained in (d-2) as PCR products, and a PCR product m8D-FL having m8D-F and m8D-S linked together was obtained.

(d-4) The PCR product m8D-FL obtained in (d-3) was used as a template, and PCR was performed using the same method as in (a-4) other than using oligonucleotides consisting of the sequences set forth in SEQ ID NO: 8 and SEQ ID NO: 9 as PCR primers. Thereby, a polynucleotide encoding FcγRIIa-m8D was prepared.

(d-5) The polynucleotide obtained in (d-4) was purified, digested with the restriction enzymes NcoI and HindIII, and then ligated into the expression vector pETMalE (Japanese Unexamined Patent Publication (Kokai) No. 2011-206046) which had been digested with the restriction enzymes NcoI and HindIII beforehand. This was used to transform *E. coli* BL21 (DE3).

(d-6) The obtained transformants were cultured in LB culture medium to which 50 μg/mL of kanamycin had been added. By extracting plasmids from the harvested bacteria (transformants) the plasmid pET-FcγRIIa-mD8 containing a polynucleotide encoding FcγRIIa-mD8 which is a polynucleotide with an additional amino acid substitution at one site with respect to FcγRIIa-m7 was obtained.

(d-7) Sequence analysis of the nucleotide sequence of pET-FcγRIIa-mD8 was performed using the same method as in EXAMPLE 2 (6).

The amino acid sequence of the FcγRIIa-m8D to which a signal sequence and a polyhistidine tag have been added is set forth in SEQ ID NO: 17 and the polynucleotide sequence encoding this FcγRII-m8D is set forth in SEQ ID NO: 16. Note that in SEQ ID NO: 17, the methionine (Met) at position 1 to the alanine (Ala) at position 26 constitute a MalE signal peptide, the methionine (Met) at position 27 and the glycine (Gly) at position 28 constitute a linker sequence, the glutamine (Gln) at position 29 to the glutamine (Gln) at position 201 constitute the FcγRIIa-m8D amino acid sequence (corresponding to the region of SEQ ID NO: 1 from position 34 to position 206), the glycines (Gly) at position 202 and position 203 constitute a linker sequence, and the histidines (His) from position 204 to position 209 constitute a tag sequence.

Example 4 Evaluation of Acid Stability of Fc-Binding Protein (1)

(1) The transformants for expressing FcγRII-m6, as well FcγRII-m8A, FcγRII-m8B, FcγRII-m8C, and FcγRII-m8D prepared in EXAMPLE 3 were each precultured by inoculation into 3 mL of 2YT liquid medium (peptone: 16 g/L, yeast extract: 10 g/L, sodium chloride: 5 g/L) containing 50 μg/mL of kanamycin and then aerobic shake culturing overnight at 37° C.

(2) 200 μL of the preculture solution was inoculated into 20 mL of 2YT liquid medium to which 50 μg/mL of kanamycin had been added, then aerobically shake cultured at 37° C.

(3) 1.5 hours after culturing had been started, the culturing temperature was changed to 20° C. followed by shake culturing for 30 minutes. IPTG was then added to a final concentration of 0.01 mM, then shake culturing was continued aerobically overnight at 20° C.

(4) Following completion of culturing, the bacterial cells were harvested by centrifugation to prepare a protein extract solution using the BugBuster Protein Extraction Kit (Takara Bio).

(5) The antibody binding activities of FcγRIIa-m6, FcγRIIa-m8A, FcγRIIa-m8B, FcγRIIa-m8C, and FcγRIIa-m8D in the protein extract prepared in (4) were measured using the ELISA method described in (4) of EXAMPLE 2. At this time, protein concentrations were measured by preparing a calibration curve using the purified and quantified FcγRIIa-m6.

(6) Each of the Fc-binding proteins was diluted to a concentration of 10 μg/mL with pure water, then acid treatment was performed thereon by mixing 50 μL of the above diluted solutions and 50 μL of 20 mM glycine-hydrochloric acid buffer solution (pH 3.0) and leaving the mixture to stand for 24 hours at 30° C. Thereafter, the mixture was neutralized with a four-fold dilution with 1 M Tris-hydrochloric acid buffer solution (pH 7.0) and the binding activity of the Fc-binding protein was measured using the ELISA method described in EXAMPLE 2 (4).

(7) The residual activity was calculated by dividing the antibody binding activity when acid treatment was performed by the antibody binding activity when the acid treatment was not performed, and acid stability was evaluated.

The results are illustrated in Table 5. Among the Fc-binding proteins prepared in EXAMPLE 3, since FcγRIIa-m8B and FcγRIIa-m8D had a higher residual activity than FcγRIIa-m6, it was confirmed that the acid stability of FcγRIIa-m8B and FcγRIIa-m8D had been improved compared to FcγRIIa-m6.

TABLE 5

| EXAMPLE | NAME | SEQ ID NO | RESIDUAL ACTIVITY [%] |
|---|---|---|---|
| EXAMPLE 3(a) | FcγRIIa-m8A | 11 | 55.7 |
| EXAMPLE 3(b) | FcγRIIa-m8B | 13 | 73.5 |
| EXAMPLE 3(c) | FcγRIIa-m8C | 15 | 25.2 |
| EXAMPLE 3(d) | FcγRIIa-m8D | 17 | 73.8 |
| | FcγRIIa-m6 | 3 | 56.9 |

Example 5 Introduction of Further Amino Acid Substitutions (2)

The amino acid substitutions involved in improving the acid stability of the Fc-binding protein found in EXAMPLE 2 were further introduced into FcγRIIa-m8D to further improve the acid stability. Introduction (accumulation) of amino acid substitutions was mainly carried out using PCR and the three types of polypeptides shown in (a) to (c) below were prepared.

(a) a polypeptide (named FcγRIIa-m10A) wherein an Ile45Thr and a Gln69Leu acid amino substitution were further introduced to FcγRIIa-m8D, (b) a polypeptide (named FcγRIIa-m10B) wherein an Ile45Thr and a Pro83Leu amino acid substitution were further introduced to FcγRIIa-m8D, (c) a polypeptide (named FcγRIIa-m10C) wherein a Gln69Leu and a Pro83Leu amino acid substitution were further introduced to FcγRIIa-m8D.

The method for preparing each Fc-binding protein is described in detail below.

(a) FcγRIIa-m10A

Ile45Thr and Gln69Leu were selected from among the amino acid substitutions contributing to improved acid stability elucidated in EXAMPLE 2 and were accumulated in FcγRIIa-m8D to prepare FcγRIIa-m10A. Specifically, mutations causing Ile45Thr and Gln69Leu were introduced to the polynucleotide encoding FcγRIIa-m8D obtained in EXAMPLE 3 (d) to prepare FcγRIIa-m10A.

(a-1) The polynucleotide (SEQ ID NO: 16) encoding the Fc-binding protein comprising FcγRIIa-m8D obtained in EXAMPLE 3 (d) was used as a template, and PCR and PCR product purification were performed using the same methods as in EXAMPLE 3 (a-1) other than using oligonucleotides consisting of the sequences set forth in SEQ ID NO: 8 and SEQ ID NO: 27 as PCR primers. The purified PCR product was named m10A-F.

(a-2) Using the same polynucleotide as in (a-1) as a template, PCR and PCR product purification were performed using the same methods as in EXAMPLE 3 (a-1) other than using oligonucleotides consisting of the sequences set forth in SEQ ID NO: 26 and SEQ ID NO: 29 as PCR primers. The purified PCR product was named m10A-S.

(a-3) Using the same polynucleotide as in (a-1) as a template, PCR and PCR product purification were performed using the same methods as in EXAMPLE 3 (a-1) other than using oligonucleotides consisting of the sequences set forth in SEQ ID NO: 28 and SEQ ID NO: 9 as PCR primers. The purified PCR product was named m10A-T.

(a-4) PCR was performed using the same method as in EXAMPLE 3 (a-3), other than using m10A-F obtained in (a-1), m10A-S obtained in (a-2), and m10A-T obtained in (a-3) as PCR products, and the PCR product m10-FL having m10A-F, m10A-S, and m10A-T linked together was obtained.

(a-5) The PCR product m10A-FL obtained in (a-4) was used as a template, and PCR was performed using the same method as in EXAMPLE 3 (a-4) other than using oligonucleotides consisting of the sequences set forth in SEQ ID NO: 8 and SEQ ID NO: 9 as PCR primers. Thereby, a polynucleotide encoding FcγRIIa-m10A was prepared.

(a-6) The polynucleotide obtained in (a-5) was purified, digested with the restriction enzymes NcoI and HindIII, and then ligated into the expression vector pETMalE (Japanese Unexamined Patent Publication (Kokai) No. 2011-206046) which had been digested with NcoI and HindIII beforehand. This was used to transform *E. coli* BL21 (DE3).

(a-7) The obtained transformants were cultured in LB culture medium to which 50 μg/mL of kanamycin had been added. By extracting plasmids from the harvested bacteria (transformants) the plasmid pET-FcγRIIa-m10A containing a polynucleotide encoding FcγRIIa-m10A which is a polynucleotide with additional amino acid substitutions at three sites with respect to FcγRIIa-m7 was obtained.

(a-8) Sequence analysis of the nucleotide sequence of pET-FcγRIIa-m10A was performed using the same method as in EXAMPLE 2 (6).

The amino acid sequence of FcγRIIa-m10A to which a signal sequence and a polyhistidine tag have been added is set forth in SEQ ID NO: 19 and the polynucleotide sequence encoding this FcγRIIa-m10A is set forth in SEQ ID NO: 18. Note that in SEQ ID NO: 19, the methionine (Met) at position 1 to the alanine (Ala) at position 26 constitute a MalE signal peptide, the methionine (Met) at position 27 and the glycine (Gly) at position 28 constitute a linker sequence, the glutamine (Gln) at position 29 to the glutamine (Gln) at position 201 constitute the FcγRIIa-m10A amino acid sequence (corresponding to the region of SEQ ID NO: 1 from position 34 to position 206), the glycines (Gly) at position 202 and position 203 constitute a linker sequence, and the histidines (His) from position 204 to position 209 constitute a tag sequence.

(b) FcγRIIa-m10B

Ile45Thr and Pro83Leu were selected from among the amino acid substitutions contributing to improved acid stability elucidated in EXAMPLE 2 and were accumulated in FcγRIIa-m8D to prepare FcγRIIa-m10B. Specifically, mutations causing Ile45Thr and Pro83Leu were introduced to the polynucleotide encoding FcγRIIa-m8D obtained in EXAMPLE 3(d) to prepare FcγRIIa-m10B.

(b-1) The polynucleotide (SEQ ID NO: 16) encoding the Fc-binding protein comprising FcγRIIa-m8D obtained in EXAMPLE 3(d) was used as a template, and PCR and PCR product purification were performed using the same methods as in EXAMPLE 3 (a-1) other than using oligonucleotides consisting of the sequences set forth in SEQ ID NO: 8 and SEQ ID NO: 27 as PCR primers. The purified PCR product was named m10B-F.

(b-2) Using the same polynucleotide as in (b-1) as a template, PCR and PCR product purification were performed using the same methods as in EXAMPLE 3 (a-1) other than using oligonucleotides consisting of the sequences set forth in SEQ ID NO: 26 and SEQ ID NO: 31 as PCR primers. The purified PCR product was named m10B-S.

(b-3) Using the same polynucleotide as in (b-2) as a template, PCR and PCR product purification were performed using the same methods as in EXAMPLE 3 (a-1) other than using oligonucleotides consisting of the sequences set forth in SEQ ID NO: 30 and SEQ ID NO: 9 as PCR primers. The purified PCR product was named m10B-T.

(b-4) PCR was performed using the same method as in EXAMPLE 3 section (a-3) other than using m10B-F obtained in (b-1), m10B-S obtained in (b-2), and m10B-T obtained in (b-3) as PCR products, and the PCR product m10B-FL having m10B-F, m10B-S, and m10B-T linked together was obtained.

(b-5) The PCR product m10B-FL obtained in (b-4) was used as a template, and PCR was performed using the same method as in EXAMPLE 3 section (a-4) other than using oligonucleotides consisting of the sequences set forth in SEQ ID NO: 8 and SEQ ID NO: 9 as PCR primers. Thereby, a polynucleotide encoding FcγRIIa-m10B was prepared.

(b-6) The polynucleotide obtained in (b-5) was purified, digested with the restriction enzymes NcoI and HindIII, and then ligated into the expression vector pETMalE (Japanese Unexamined Patent Publication (Kokai) No. 2011-206046) which had been digested with NcoI and HindIII beforehand. This was used to transform *E. coli* BL21 (DE3).

(b-7) The obtained transformants were cultured in LB culture medium to which 50 μg/mL of kanamycin had been added. By extracting plasmids from the harvested bacteria (transformants) the plasmid pET-FcγRIIa-m10B containing a polynucleotide encoding FcγRIIa-m10B which is a polypeptide with additional amino acid substitutions at three sites with respect to FcγRIIa-m7 was obtained.

(b-8) Sequence analysis of the nucleotide sequence of pET-FcγRIIa-m10B was performed using the same method as in EXAMPLE 2 (6).

The amino acid sequence of the FcγRIIa-m10B to which a signal sequence and a polyhistidine tag have been added is set forth in SEQ ID NO: 21 and the polynucleotide sequence encoding this FcγRIIa-m10B is set forth in SEQ ID NO: 20. Note that in SEQ ID NO: 21, the methionine (Met) at position 1 to the alanine (Ala) at position 26 constitute a MalE signal peptide, the methionine (Met) at position 27 and the glycine (Gly) at position 28 constitute a linker sequence, the glutamine (Gln) at position 29 to the glutamine (Gln) at position 201 constitute the FcγRIIa-m10B amino acid sequence (corresponding to the region of SEQ ID NO: 1 from position 34 to position 206), the glycines (Gly) at position 202 and position 203 constitute a linker sequence, and the histidines (His) from position 204 to position 209 constitute a tag sequence.

(c) FcγRIIa-m10C

Gln69Leu and Pro83Leu were selected from among the amino acid substitutions contributing to improved acid stability elucidated in EXAMPLE 2 and were accumulated in FcγRIIa-m8D to prepare FcγRIIa-m10C. Specifically, mutations causing Gln69Leu and Pro83Leu were introduced to the polynucleotide encoding FcγRIIa-m8D obtained in EXAMPLE 3 (d) to prepare FcγRIIa-m10C.

(c-1) The polynucleotide (SEQ ID NO: 16) encoding the Fc-binding protein comprising FcγRIIa-m8D obtained in EXAMPLE 3(d) was used as a template, and PCR and PCR product purification were performed using the same methods as in EXAMPLE 3 (a-1) other than using oligonucleotides consisting of the sequences set forth in SEQ ID NO: 8 and SEQ ID NO: 29 as PCR primers. The purified PCR product was named m10C-F.

(c-2) Using the same polynucleotide as in (c-1) as a template, PCR and PCR product purification were performed using the same methods as in EXAMPLE 3 (a-1) other than using oligonucleotides consisting of the sequences set forth in SEQ ID NO: 28 and SEQ ID NO: 31 as PCR primers. The purified PCR product was named m10C-S.

(c-3) Using the same polynucleotide as in (c-1) as a template, PCR and PCR product purification was performed with the same method as in EXAMPLE 3 (a-1) other than using oligonucleotides consisting of the sequences set forth in SEQ ID NO: 30 and SEQ ID NO: 9 as PCR primers. The purified PCR product was named m10C-T.

(c-4) PCR was performed using the same method as in EXAMPLE 3 section (a-3), other than using m10C-F obtained in (c-1), m10C-S obtained in (c-2), and m10C-T obtained in (c-3) as PCR products, and the PCR product m10C-FL having m10C-F, m10C-S, and m10C-T linked together was obtained.

(c-5) The PCR product m10C-FL obtained in (c-4) was used as a template, and PCR was performed using the same method as in EXAMPLE 3 section (a-4) other than using oligonucleotides consisting of the sequences set forth in SEQ ID NO: 8 and SEQ ID NO: 9 as PCR primers. Thereby, a polynucleotide encoding FcγRIIa-m10C was prepared.

(c-6) The polynucleotide obtained in (c-5) was purified, digested with the restriction enzymes NcoI and HindIII, and then ligated into the expression vector pETMalE (Japanese Unexamined Patent Publication (Kokai) No. 2011-206046) which had been digested with the restriction enzymes NcoI and HindIII beforehand. This was used to transform *E. coli* BL21 (DE3).

(c-7) The obtained transformants were cultured in LB culture medium to which 50 μg/mL of kanamycin had been added. By extracting plasmids from the harvested bacteria (transformants) the plasmid pET-FcγRIIa-m10C containing a polynucleotide encoding FcγRIIa-m10C which is a polypeptide with additional amino acid substitutions at three sites with respect to FcγRIIa-m7 was obtained.

(c-8) Sequence analysis of the nucleotide sequence of pET-FcγRIIa-m10C was performed using the same method as in EXAMPLE 2 (6).

The amino acid sequence of the FcγRIIa-m10C to which a signal sequence and a polyhistidine tag have been added is set forth in SEQ ID NO: 23 and the polynucleotide sequence encoding this FcγRIIa-m10C is set forth in SEQ ID NO: 22. Note that in SEQ ID NO: 23, the methionine (Met) at position 1 to the alanine (Ala) at position 26 constitute a MalE signal peptide, the methionine (Met) at position 27 and the glycine (Gly) at position 28 constitute a linker sequence, the glutamine (Gln) at position 29 to the glutamine (Gln) at position 201 constitute the FcγRIIa-m10C amino acid sequence (corresponding to the region of SEQ ID NO: 1 from position 34 to position 206), the glycines (Gly) at position 202 and position 203 constitute a linker sequence, and the histidines (His) from position 204 to position 209 constitute a tag sequence.

Example 6 Introduction of Further Amino Acid Substitutions (3)

Ile45Thr, Gln69Leu, and Pro83Leu were selected from among the amino acid substitutions involved in improving the acid stability of the Fc-binding protein elucidated in EXAMPLE 2, and further introduced into FcγRIIa-m8D to further improve the acid stability. Specifically, a mutation causing Pro83Leu was introduced to the polynucleotide encoding FcγRIIa-m10A obtained in EXAMPLE 5 (a) to prepare a protein (named FcγRIIa-m11). The method of preparing FcγRIIa-m11 is described in detail below.

(1) The polynucleotide (SEQ ID NO: 18) encoding the Fc-binding protein comprising FcγRIIa-m10A obtained in EXAMPLE 5(a) was used as a template, and PCR and PCR product purification were performed using the same methods as in EXAMPLE 3 (a-1) other than using oligonucleotides consisting of the sequences set forth in SEQ ID NO: 8 and SEQ ID NO: 31 as PCR primers. The purified PCR product was named m11-F.

(2) Using the same polynucleotide as in (1) as a template, PCR and PCR product purification were performed using the same methods as in EXAMPLE 3 (a-1) other than using oligonucleotides consisting of the sequences set forth in SEQ ID NO: 30 and SEQ ID NO: 9 as PCR primers. The purified PCR product was named m11-S (3) PCR was performed using the same method as in EXAMPLE 3 section (a-3) other than using m11-F obtained in (1) and m11-S obtained in (2) as PCR products, and the PCR product m11-FL having m11-F and m11-S linked together was obtained.

(4) The PCR product m11-FL obtained in (3) was used as a template, and PCR was performed using the same method as in EXAMPLE 3 section (a-4) other than using oligonucleotides consisting of the sequences set forth in SEQ ID NO: 8 and SEQ ID NO: 9 as PCR primers. Thereby, a polynucleotide encoding FcγRIIa-m11 was prepared.

(5) The polynucleotide obtained in (4) was purified, digested with the restriction enzymes NcoI and HindIII, and then ligated into the expression vector pETMalE (Japanese Unexamined Patent Publication (Kokai) No. 2011-206046) which had been digested with the restriction enzymes NcoI and HindIII beforehand. This was used to transform *E. coli* BL21 (DE3).

(6) The obtained transformants were cultured in LB culture medium to which 50 μg/mL of kanamycin had been added. By extracting plasmids from the harvested bacteria (transformants) the plasmid pET-FcγRIIa-m11 containing a polynucleotide encoding FcγRIIa-m11 which is a polynucleotide with additional amino acid substitutions at four sites with respect to FcγRIIa-m7 was obtained.

(7) Sequence analysis of the nucleotide sequence of pET-FcγRIIa-m11 was performed using the same method as in EXAMPLE 2 (6).

The amino acid sequence of the FcγRIIa-m11 to which a signal sequence and a polyhistidine tag have been added is set forth in SEQ ID NO: 25 and the polynucleotide sequence encoding this FcγRIIa-m11 is set forth in SEQ ID NO: 24. Note that in SEQ ID NO: 25, the methionine (Met) at position 1 to the alanine (Ala) at position 26 constitute a MalE signal peptide, the methionine (Met) at position 27 and the glycine (Gly) at position 28 constitute a linker sequence, the glutamine (Gln) at position 29 to the glutamine (Gln) at position 201 constitute the FcγRIIa-m11 amino acid sequence (corresponding to the region of SEQ ID NO: 1 from position 34 to position 206), the glycines (Gly) at position 202 and position 203 constitute a linker sequence, and the histidines (His) from position 204 to position 209 constitute a tag sequence.

Example 7 Evaluation of Acid Stability of Fc-Binding Protein (2)

(1) The transformants for expressing FcγRIIa-m6, as well as FcγRIIa-m10A, FcγRIIa-m10B, and FcγRIIa-m10C prepared in EXAMPLE 5, in addition to FcγRIIa-m11 prepared in EXAMPLE 6, were cultured and the proteins prepared by extraction therefrom using the same method as in EXAMPLE 4 (1) to (4).

(2) The antibody binding activities of FcγRIIa-m6, the three types of FcγRIIa-m10, and FcγRIIa-m11 in the protein extract solution prepared in (1) were measured using the ELISA method described in Example 2 (4). At this time, protein concentrations were measured by preparing a calibration curve using the purified and quantified FcγRIIa-m6.

(3) Each of the Fc-binding proteins was diluted to a concentration of 10 μg/mL with pure water, then acid treatment was performed thereon by mixing 50 μL of the above diluted solution and 50 μL of 20 mM glycine-hydrochloric acid buffer solution (pH 3.0), and leaving the mixture to stand for 24 hours at 30° C. Thereafter, the mixture was neutralized with a four-fold dilution with 1 M Tris-hydrochloric acid buffer solution (pH 7.0) and the antibody binding activity of the Fc-binding protein was measured using the ELISA method described in Example 2 (4).

(4) The residual activity was calculated by dividing the antibody binding activity when acid treatment was performed by the antibody binding activity when the acid treatment was not performed, and acid stability was evaluated.

The results are illustrated in Table 6. Since FcγRIIa-m10A, FcγRIIa-m10C, and FcγRIIa-m11 had a higher residual activity than FcγRIIa-m6, it was confirmed that the acid stability of these proteins had been improved compared to FcγRIIa-m6. Thereamong, since FcγRIIa-m11 had a high residual activity of 95.3%, FcγRIIa-m11 was considered to be an Fc binding protein having particularly improved acid stability.

TABLE 6

| EXAMPLE | NAME | SEQ ID NO | RESIDUAL ACTIVITY [%] |
|---|---|---|---|
| EXAMPLE 5(a) | FcγRIIa-m10A | 19 | 77.3 |
| EXAMPLE 5(b) | FcγRIIa-m10B | 21 | 46.9 |
| EXAMPLE 5(c) | FcγRIIa-m10C | 23 | 72.9 |
| EXAMPLE 6 | FcγRIIa-m11 | 25 | 95.3 |
|  | FcγRIIa-m6 | 3 | 56.9 |

Example 8 Deletion of Amino Acid Residues in Loop Region

In order to further improve acid stability, amino acid residues positioned in the loop region of FcγRIIa were deleted on the basis of knowledge of crystal structure data of FcγRIIa registered in public databases (PDB ID: 1FCG). Specifically, some or all amino acid residues in the loop region (the glutamine at position 58 to the serine at position 67 of SEQ ID NO: 25) were deleted from the FcγRIIa-m11 protein obtained in EXAMPLE 6 to prepare the Fc-binding proteins indicated in (a) to (j) below by the following method.

a) an Fc-binding protein wherein the serine at position 62 of FcγRIIa-m11 was deleted (named FcγRII-m11-Del1)

b) an Fc-binding protein wherein the serine at position 62 and the glutamic acid in position 64 of FcγRIIa-m11 were deleted (named FcγRII-m11-Del2)

c) an Fc-binding protein wherein the amino acid residues from the serine at position 62 to the glutamic acid in position 64 of FcγRIIa-m11 were deleted (named FcγRII-m11-Del3), d) an Fc-binding protein wherein the amino acid residues from the arginine at position 61 to the glutamic acid at position 64 of FcγRIIa-m11 were deleted (named FcγRII-m11-Del4), e) an Fc-binding protein wherein the amino acid residues from the arginine at position 61 to the serine at position 65 of FcγRIIa-m11 were deleted (named FcγRII-m11-Del5), f) an Fc-binding protein wherein the amino acid residues from the arginine at position 60 to the serine at position 65 of FcγRIIa-m11 were deleted (named FcγRII-m11-Del6), g) an Fc-binding protein wherein the amino acid residues from the glycine at position 59 to the serine at position 65 of FcγRIIa-m11 were deleted (named FcγRII-m11-Del7), h) an Fc-binding protein wherein the amino acid residues from the glycine at position 59 to the aspartic acid at position 66 of FcγRIIa-m11 were deleted (named FcγRII-m11-Del8), i) an Fc-binding protein wherein the amino acid residues from the glycine at position 59 to the serine at position 67 of FcγRIIa-m11 were deleted (named FcγRII-m11-Del9), j) an Fc-binding protein wherein the amino acid residues from the glutamine at position 58 to the serine at position 67 of FcγRIIa-m11 were deleted (named FcγRII-m11-Del10).

(1) Polypeptides comprising the above 10 types of Fc-binding protein deletion ((a) FcγRII-m11-Del1: SEQ ID NO: 34, (b) FcγRII-m11-Del2: SEQ ID NO: 36, (c) FcγRII-m11-Del3: SEQ ID NO: 38, (d) FcγRIIa-m11-Del4: SEQ ID NO: 40, (e) FcγRII-m11-Del5: SEQ ID NO: 42, (f) FcγRII-m11-Del6: SEQ ID NO: 44, (g) FcγRII-m11-Del7: SEQ ID NO: 46, (h) FcγRII-m11-Del8: SEQ ID NO: 48, (i) FcγRII-m11-Del9: SEQ ID NO: 50, and (j) FcγRII-m11-Del10: SEQ ID NO: 52) were prepared by artificial gene synthesis (carried out by FASMAC).

(2) The polynucleotides prepared in (1) were ligated into the expression vector pETMalE (Japanese Unexamined Patent Publication (Kokai) No. 2011-206046) which had been digested with the restriction enzymes NcoI and HindIII. These were used to transform *E. coli* BL21 (DE3).

(3) The resulting transformants were cultured and the proteins prepared by extraction therefrom using the same method as in EXAMPLE 4 (1) to (4).

The amino acid sequence of (a) FcγRIIa-m11-Del1 to which a signal sequence and a polyhistidine tag have been added is set forth in SEQ ID NO: 35, the amino acid sequence of (b) FcγRIIa-m11-Del2 to which a signal sequence and a polyhistidine tag have been added is set forth in SEQ ID NO: 37, the amino acid sequence of (c) FcγRIIa-m11-Del3 to which a signal sequence and a polyhistidine tag has been added is set forth in SEQ ID NO: 39, the amino acid sequence of (d) FcγRIIa-m11-Del4 to which a signal sequence and a polyhistidine tag have been added is set forth in SEQ ID NO: 41, the amino acid sequence of (e) FcγRIIa-m11-Del5 to which a signal sequence and a polyhistidine tag have been added is set forth in SEQ ID NO: 43, the amino acid sequence of (f) FcγRIIa-m11-Del6 to which a signal sequence and a polyhistidine tag have been added is set forth in SEQ ID NO: 45, the amino acid sequence of (g) FcγRIIa-m11-Del7 to which a signal sequence and a polyhistidine tag have been added is set forth in SEQ ID NO: 47, the amino acid sequence of (h) FcγRIIa-m11-Del8 to which a signal sequence and a polyhistidine tag have been added is set forth in SEQ ID NO: 49, the amino acid sequence of (i) FcγRIIa-m11-Del9 to which a signal sequence and a polyhistidine tag have been added is set forth in SEQ ID NO: 51, the amino acid sequence of (j) FcγRIIa-m11-Del10 to which a signal sequence and a polyhistidine tag have been added is set forth in SEQ ID NO: 53. Note that in these sequences, the methionine (Met) at position 1 to the alanine (Ala) at position 26 constitute a MalE signal peptide, the methionine (Met) at position 27 and the glycine (Gly) at position 28 constitute a linker sequence, the six histidine (His) residues at the C-terminal side constitute a tag sequence, the glycines (Gly) at position 7 and position 8 from the C-terminal side constitute a linker sequence, other regions constitute polypeptides capable of binding to the Fc region (FcγRIIa-m11-Del1, FcγRIIa-m11-Del2, FcγRIIa-m11-Del3, FcγRIIa-m11-Del4, FcγRIIa-m11-Del5, FcγRIIa-m11-Del6, FcγRIIa-m11-Del7, FcγRIIa-m11-Del8, FcγRIIa-m11-Del9, or FcγRIIa-m11-Del10).

Example 9 Evaluation of Acid Stability of Fc-Binding Protein (3)

(1) Transformants for expressing FcγRIIa-m11 prepared in EXAMPLE 6 were cultured and the proteins prepared by extraction therefrom using the same method as in EXAMPLE 4 (1) to (4).

(2) The antibody binding activities in the protein extract solution prepared in (1) and EXAMPLE 8 were measured using the ELISA method described in Example 2 (4). At this time, protein concentrations were measured by preparing a calibration curve using the purified and quantified FcγRIIa-m6. Note that the protein concentrations of FcγRIIa-m11-Del8, FcγRIIa-m11-Del9, and FcγRIIa-m11-Del10 could not be measured due to insufficient protein expression.

(3) Each of the Fc-binding proteins was diluted to a concentration of 10 μg/mL with pure water, then acid treatment was performed thereon by mixing 50 μL of the diluted solution and 50 μL of 20 mM glycine-hydrochloric acid buffer solution (pH 3.0), and leaving the mixture to stand for 72 hours at 30° C. Thereafter, the mixture was neutralized with a four-fold dilution with 1 M Tris-hydrochloric acid buffer solution (pH 7.0) and the antibody binding activity of the Fc-binding protein was measured using the ELISA method described in section (4) of Example 2.

(4) The residual activity was calculated by dividing the antibody binding activity when acid treatment was performed by the antibody binding activity when the acid treatment was not performed, and acid stability was evaluated.

The results are illustrated in Table 7. Since FcγRIIa-m11-Del1 and FcγRIIa-m11-Del5 had a higher residual activity than FcγRIIa-m11 72 hours after treatment, it was confirmed that the acid stability of these proteins had been improved compared to FcγRIIa-m11.

TABLE 7

| EXAMPLE | NAME | SEQ ID NO | RESIDUAL ACTIVITY [%] |
|---|---|---|---|
| EXAMPLE 7 (a) | FcγRIIa-m11-Del1 | 35 | 89.8 |
| EXAMPLE 7 (b) | FcγRIIa-m11-Del2 | 37 | 81.3 |
| EXAMPLE 7 (c) | FcγRIIa-m11-Del3 | 39 | 72.4 |
| EXAMPLE 7 (d) | FcγRIIa-m11-Del4 | 41 | 76.7 |
| EXAMPLE 7 (e) | FcγRIIa-m11-Del5 | 43 | 86.5 |
| EXAMPLE 7 (f) | FcγRIIa-m11-Del6 | 45 | 25.4 |
| EXAMPLE 7(g) | FcγRIIa-m11-Del7 | 47 | 33.3 |
| EXAMPLE 7(h) | FcγRIIa-m11-Del8 | 49 | — |
| EXAMPLE 7(i) | FcγRIIa-m11-Del9 | 51 | — |
| EXAMPLE 7(j) | FcγRIIa-m11-Del10 | 53 | — |
| EXAMPLE 6 | FcγRIIa-m11 | 25 | 83.6 |

The present invention is described above in detail with reference to specific embodiments. However, it is apparent to those skilled in the art that various changes and modifications can be made without departing from the spirit and scope of the invention.

Note that the entire contents of the specification, sequence listing, claims, drawings and abstracts of Japanese patent application 2018-029994 filed on Feb. 22, 2018, Japanese patent application 2018-154007 filed on Aug. 20, 2018, and Japanese patent Application 2019-003038 filed on Jan. 11, 2019 are incorporated herein by reference.

The invention claimed is:

1. An Fc-binding protein, comprising:

at least amino acid residues from glutamine at position 29 to glutamine at position 201 of the amino acid sequence set forth in SEQ ID NO: 2, with the proviso that the Fc-binding protein is modified with (i) amino acid modifications at the 6 positions indicated below:

a substitution of isoleucine to valine at position 68 of SEQ ID NO: 2, a substitution of histidine to glutamine at position 80 of SEQ ID NO: 2, a substitution of serine to threonine at position 84 of SEQ ID NO: 2, a substitution of asparagine to threonine at position 90 of SEQ ID NO: 2, a substitution of asparagine to serine at position 91 of SEQ ID NO: 2, and a substitution of histidine to arginine at position 125 of SEQ ID NO: 2, and (ii) the amino acid modification indicated (1) below:

(1) a substitution of leucine to serine at position 190 of SEQ ID NO: 2, and optionally, one or more of the modifications indicated in (2) to (12) below:

(2) a substitution of isoleucine to threonine at position 45 of SEQ ID NO: 2, (3) a substitution of glutamine to leucine at position 69 of SEQ ID NO: 2, (4) a substitution of proline to leucine at position 83 of SEQ ID NO: 2, (5) a substitution of threonine to proline at position 123 of SEQ ID NO: 2, (6) a substitution of proline to glutamine at position 42 of SEQ ID NO: 2, (7) a substitution of proline to leucine at position 63 of SEQ ID NO: 2, (8) a substitution of asparagine to serine at position 75 of SEQ ID NO: 2, (9) a substitution of leucine to histidine at position 163 of SEQ ID NO: 2,

(10) a substitution of aspartic acid to valine at position 179 of SEQ ID NO: 2,

(11) a substitution of isoleucine to valine at position 198 of SEQ ID NO: 2, and

(12) a deletion of serine at position 62 of SEQ ID NO: 2.

2. The Fc-binding protein according to claim 1, wherein the Fc-binding protein is an Fc-binding protein comprising at least amino acid residues from glutamine at position 29 to glutamine at position 201 of the amino acid sequence set forth in any of SEQ ID NOs: 5, 13, 17, 19, 23, and 25.

3. A polynucleotide encoding the Fc-binding protein according to claim 1.

4. An expression vector comprising the polynucleotide according to claim 3.

5. A transformant comprising a host with the recombinant vector according to claim 4 which produces the Fc-binding protein.

6. The transformant according to claim 5, wherein the host is *Escherichia coli*.

7. A method for producing the Fc-binding protein, comprising: producing the Fc-binding protein by culturing the transformant according to claim 5; and harvesting the Fc-binding protein from the obtained culture product.

8. An antibody adsorbent obtained by immobilizing the Fc-binding protein according to claim 1 on an insoluble carrier.

9. An antibody separation method comprising: adding a solution containing an antibody to a column filled with the adsorbent according to claim 8 and adsorbing the antibody to the adsorbent; and eluting the antibody adsorbed to the adsorbent using an eluent.

10. An Fc-binding protein, comprising:

at least amino acid residues from glutamine at position 29 to glutamine at position 201 of the amino acid sequence set forth in SEQ ID NO: 2, with the proviso that the Fc-binding protein is modified with (i) amino acid modifications at the 6 positions indicated below:

a substitution of isoleucine to valine at position 68 of SEQ ID NO: 2, a substitution of histidine to glutamine at position 80 of SEQ ID NO: 2, a substitution of serine to threonine at position 84 of SEQ ID NO: 2, a substitution of asparagine to threonine at position 90 of SEQ ID NO: 2, a substitution of asparagine to serine at position 91 of SEQ ID NO: 2, and a substitution of histidine to arginine at position 125 of SEQ ID NO: 2, and (ii) the amino acid modification indicated (1) below:

(1) a substitution of leucine to serine at position 190 of SEQ ID NO: 2, and one or more of the modifications indicated in (2) to (12) below:

(2) a substitution of isoleucine to threonine at position 45 of SEQ ID NO: 2, (3) a substitution of glutamine to leucine at position 69 of SEQ ID NO: 2, (4) a substitution of proline to leucine at position 83 of SEQ ID NO: 2, (5) a substitution of threonine to proline at position 123 of SEQ ID NO: 2, (6) a substitution of proline to glutamine at position 42 of SEQ ID NO: 2, (7) a substitution of proline to leucine at position 63 of SEQ ID NO: 2, (8) a substitution of asparagine to serine at position 75 of SEQ ID NO: 2, (9) a substitution of leucine to histidine at position 163 of SEQ ID NO: 2,

(10) a substitution of aspartic acid to valine at position 179 of SEQ ID NO: 2,

(11) a substitution of isoleucine to valine at position 198 of SEQ ID NO: 2, and

(12) a deletion of serine at position 62 of SEQ ID NO: 2.

* * * * *

SEQUENCE LISTING

```
<160> NUMBER OF SEQ ID NOS: 53

<210> SEQ ID NO 1
<211> LENGTH: 317
<212> TYPE: PRT
<213> ORGANISM: Homo sapiens
<300> PUBLICATION INFORMATION:
<308> DATABASE ACCESSION NUMBER: UniProt P12318-1
<309> DATABASE ENTRY DATE: 2007-11-13
<313> RELEVANT RESIDUES IN SEQ ID NO: (1)..(317)

<400> SEQUENCE: 1

Met Thr Met Glu Thr Gln Met Ser Gln Asn Val Cys Pro Arg Asn Leu
1               5                   10                  15
```

```
Trp Leu Leu Gln Pro Leu Thr Val Leu Leu Leu Leu Ala Ser Ala Asp
            20                  25                  30

Ser Gln Ala Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
    130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205

Ser Met Gly Ser Ser Ser Pro Met Gly Ile Ile Val Ala Val Val Ile
    210                 215                 220

Ala Thr Ala Val Ala Ala Ile Val Ala Ala Val Val Ala Leu Ile Tyr
225                 230                 235                 240

Cys Arg Lys Lys Arg Ile Ser Ala Asn Ser Thr Asp Pro Val Lys Ala
                245                 250                 255

Ala Gln Phe Glu Pro Pro Gly Arg Gln Met Ile Ala Ile Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Asp Lys Asn Ile Tyr
    290                 295                 300

Leu Thr Leu Pro Pro Asn Asp His Val Asn Ser Asn Asn
305                 310                 315


<210> SEQ ID NO 2
<211> LENGTH: 209
<212> TYPE: PRT
<213> ORGANISM: Artificial Sequence
<220> FEATURE:
<223> OTHER INFORMATION: MalE signal - FcgRIIa - 6His

<400> SEQUENCE: 2

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Ile Asn Val Leu
        35                  40                  45

Gln Glu Asp Ser Val Thr Leu Thr Cys Gln Gly Ala Arg Ser Pro Glu
    50                  55                  60
```

-continued

Ser Asp Ser Ile Gln Trp Phe His Asn Gly Asn Leu Ile Pro Thr His
65 70 75 80

Thr Gln Pro Ser Tyr Arg Phe Lys Ala Asn Asn Asn Asp Ser Gly Glu
85 90 95

Tyr Thr Cys Gln Thr Gly Gln Thr Ser Leu Ser Asp Pro Val His Leu
100 105 110

Thr Val Leu Ser Glu Trp Leu Val Leu Gln Thr Pro His Leu Glu Phe
115 120 125

Gln Glu Gly Glu Thr Ile Met Leu Arg Cys His Ser Trp Lys Asp Lys
130 135 140

Pro Leu Val Lys Val Thr Phe Phe Gln Asn Gly Lys Ser Gln Lys Phe
145 150 155 160

Ser His Leu Asp Pro Thr Phe Ser Ile Pro Gln Ala Asn His Ser His
165 170 175

Ser Gly Asp Tyr His Cys Thr Gly Asn Ile Gly Tyr Thr Leu Phe Ser
180 185 190

Ser Lys Pro Val Thr Ile Thr Val Gln Gly Gly His His His His His
195 200 205

His

<210> SEQ ID NO 3
<211> LENGTH: 209
<212> TYPE: PRT
<213> ORGANISM: Artificial Sequence
<220> FEATURE:
<223> OTHER INFORMATION: MalE signal - FcgRIIa-m6 - 6His

<400> SEQUENCE: 3

Met Lys Ile Lys Thr Gly Ala Arg Ile Leu Ala Leu Ser Ala Leu Thr
1 5 10 15

Thr Met Met Phe Ser Ala Ser Ala Leu Ala Met Gly Gln Ala Ala Ala
20 25 30

Pro Pro Lys Ala Val Leu Lys Leu Glu Pro Pro Trp Ile Asn Val Leu
35 40 45

Gln Glu Asp Ser Val Thr Leu Thr Cys Gln Gly Ala Arg Ser Pro Glu
50 55 60

Ser Asp Ser Val Gln Trp Phe His Asn Gly Asn Leu Ile Pro Thr Gln
65 70 75 80

Thr Gln Pro Thr Tyr Arg Phe Lys Ala Thr Ser Asn Asp Ser Gly Glu
85 90 95

Tyr Thr Cys Gln Thr Gly Gln Thr Ser Leu Ser Asp Pro Val His Leu
100 105 110

Thr Val Leu Ser Glu Trp Leu Val Leu Gln Thr Pro Arg Leu Glu Phe
115 120 125

Gln Glu Gly Glu Thr Ile Met Leu Arg Cys His Ser Trp Lys Asp Lys
130 135 140

Pro Leu Val Lys Val Thr Phe Phe Gln Asn Gly Lys Ser Gln Lys Phe
145 150 155 160

Ser His Leu Asp Pro Thr Phe Ser Ile Pro Gln Ala Asn His Ser His
165 170 175

Ser Gly Asp Tyr His Cys Thr Gly Asn Ile Gly Tyr Thr Leu Phe Ser
180 185 190

Ser Lys Pro Val Thr Ile Thr Val Gln Gly Gly His His His His His
195 200 205

His

<210> SEQ ID NO 4
<211> LENGTH: 627
<212> TYPE: DNA
<213> ORGANISM: Artificial Sequence
<220> FEATURE:
<223> OTHER INFORMATION: DNA encoding MalE signal - FcgRIIa-m6 - 6His

<400> SEQUENCE: 4

```
atgaaaataa aaacaggtgc acgcatcctc gcattatccg cattaacgac gatgatgttt     60

tccgcctcgg ctctcgccat gggacaagcc gcagcgcctc caaaggcggt tctgaaactg    120

gagccgccgt ggattaatgt gttgcaggaa gatagcgtga cgctgacctg ccagggagcc    180

cgtagcccgg aatcagacag cgtacagtgg tttcacaacg gcaatttgat ccccactcaa    240

acgcagccga cgtaccgttt caaagccacc agtaacgatt cgggcgaata tacctgccag    300

acaggccaga ccagcctgtc ggatccagtg cacctgaccg tgctgtcaga atggctggtg    360

ctgcaaaccc cgcgtctgga atttcaggaa ggcgaaacca taatgctgcg ttgccacagc    420

tggaaagata aaccgctggt gaaggtcacg ttcttccaga acgggaagag ccagaagttc    480

tcccatctcg acccgacttt tagcatcccc caggcgaatc atagccatag cggcgattat    540

cactgcaccg ggaatattgg gtatacgttg tttagcagca agccggttac tatcaccgtg    600

cagggcggcc atcatcatca tcatcat                                        627
```

<210> SEQ ID NO 5
<211> LENGTH: 209
<212> TYPE: PRT
<213> ORGANISM: Artificial Sequence
<220> FEATURE:
<223> OTHER INFORMATION: MalE signal - FcgRIIa-m7 - 6His

<400> SEQUENCE: 5

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Ile Asn Val Leu
        35                  40                  45

Gln Glu Asp Ser Val Thr Leu Thr Cys Gln Gly Ala Arg Ser Pro Glu
    50                  55                  60

Ser Asp Ser Val Gln Trp Phe His Asn Gly Asn Leu Ile Pro Thr Gln
65                  70                  75                  80

Thr Gln Pro Thr Tyr Arg Phe Lys Ala Thr Ser Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Thr Pro Arg Leu Glu Phe
        115                 120                 125

Gln Glu Gly Glu Thr Ile Met Leu Arg Cys His Ser Trp Lys Asp Lys
    130                 135                 140

Pro Leu Val Lys Val Thr Phe Phe Gln Asn Gly Lys Ser Gln Lys Phe
145                 150                 155                 160

Ser His Leu Asp Pro Thr Phe Ser Ile Pro Gln Ala Asn His Ser His
                165                 170                 175

Ser Gly Asp Tyr His Cys Thr Gly Asn Ile Gly Tyr Thr Ser Phe Ser
            180                 185                 190
```

```
Ser Lys Pro Val Thr Ile Thr Val Gln Gly Gly His His His His His
        195                 200                 205

His


<210> SEQ ID NO 6
<211> LENGTH: 627
<212> TYPE: DNA
<213> ORGANISM: Artificial Sequence
<220> FEATURE:
<223> OTHER INFORMATION: DNA encoding MalE signal - FcgRIIa-m7 - 6His

<400> SEQUENCE: 6

atgaaaataa aaacaggtgc acgcatcctc gcattatccg cattaacgac gatgatgttt      60

tccgcctcgg ctctcgccat gggacaagcc gcagcgcctc caaaggcggt tctgaaactg     120

gagccgccgt ggattaatgt gttgcaggaa gatagcgtga cgctgacctg ccagggagcc     180

cgtagcccgg aatcagacag cgtacagtgg tttcacaacg gcaatttgat ccccactcaa     240

acgcagccga cgtaccgttt caaagccacc agtaacgatt cgggcgaata tacctgccag     300

acaggccaga ccagcctgtc ggatccagtg cacctgaccg tgctgtcaga atggctggtg     360

ctgcaaaccc cgcgtctgga atttcaggaa ggcgaaacca taatgctgcg ttgccacagc     420

tggaaagata aaccgctggt gaaggtcacg ttcttccaga acgggaagag ccagaagttc     480

tcccatctcg acccgacttt tagcatcccc caggcgaatc atagccatag cggcgattat     540

cactgcaccg ggaatattgg gtatacgtcg tttagcagca agccggttac tatcaccgtg     600

cagggcggcc atcatcatca tcatcat                                         627


<210> SEQ ID NO 7
<211> LENGTH: 209
<212> TYPE: PRT
<213> ORGANISM: Artificial Sequence
<220> FEATURE:
<223> OTHER INFORMATION: MalE signal - FcgRIIa-m1 - 6His

<400> SEQUENCE: 7

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Ile Asn Val Leu
        35                  40                  45

Gln Glu Asp Ser Val Thr Leu Thr Cys Gln Gly Ala Arg Ser Pro Glu
    50                  55                  60

Ser Asp Ser Ile Gln Trp Phe His Asn Gly Asn Leu Ile Pro Thr His
65                  70                  75                  80

Thr Gln Pro Ser Tyr Arg Phe Lys Ala Asn Asn Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Thr Pro His Leu Glu Phe
        115                 120                 125

Gln Glu Gly Glu Thr Ile Met Leu Arg Cys His Ser Trp Lys Asp Lys
    130                 135                 140

Pro Leu Val Lys Val Thr Phe Phe Gln Asn Gly Lys Ser Gln Lys Phe
145                 150                 155                 160

Ser His Leu Asp Pro Thr Phe Ser Ile Pro Gln Ala Asn His Ser His
                165                 170                 175
```

Ser Gly Asp Tyr His Cys Thr Gly Asn Ile Gly Tyr Thr Ser Phe Ser
180 185 190

Ser Lys Pro Val Thr Ile Thr Val Gln Gly Gly His His His His His
195 200 205

His

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
taatacgact cactataggg 20

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide

<400> SEQUENCE: 9
atgctagtta ttgctcagcg g 21

<210> SEQ ID NO 10
<211> LENGTH: 630
<212> TYPE: DNA
<213> ORGANISM: Artificial Sequence
<220> FEATURE:
<223> OTHER INFORMATION: DNA encoding MalE signal - FcgRIIa-m8a (I45T) - 6His

<400> SEQUENCE: 10
atgaaaataa aaacaggtgc acgcatcctc gcattatccg cattaacgac gatgatgttt 60
tccgcctcgg ctctcgccat gggacaagcc gcagcgcctc caaaggcggt tctgaaactg 120
gagccgccgt ggaccaatgt gttgcaggaa gatagcgtga cgctgacctg ccagggagcc 180
cgtagcccgg aatcagacag cgtacagtgg tttcacaacg gcaatttgat ccccactcaa 240
acgcagccga cgtaccgttt caaagccacc agtaacgatt cgggcgaata tacctgccag 300
acaggccaga ccagcctgtc ggatccagtg cacctgaccg tgctgtcaga atggctggtg 360
ctgcaaaccc cgcgtctgga atttcaggaa ggcgaaacca taatgctgcg ttgccacagc 420
tggaaagata aaccgctggt gaaggtcacg ttcttccaga acgggaagag ccagaagttc 480
tcccatctcg acccgacttt tagcatcccc caggcgaatc atagccatag cggcgattat 540
cactgcaccg ggaatattgg gtatacgtct tttagcagca agccggttac tatcaccgtg 600
cagggcggcc atcatcatca tcatcattaa 630

<210> SEQ ID NO 11
<211> LENGTH: 209
<212> TYPE: PRT
<213> ORGANISM: Artificial Sequence
<220> FEATURE:
<223> OTHER INFORMATION: MalE signal - FcRIIa-m8A (I45T) - 6His

<400> SEQUENCE: 11

Met Lys Ile Lys Thr Gly Ala Arg Ile Leu Ala Leu Ser Ala Leu Thr
1 5 10 15

```
Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Thr Asn Val Leu
        35                  40                  45

Gln Glu Asp Ser Val Thr Leu Thr Cys Gln Gly Ala Arg Ser Pro Glu
    50                  55                  60

Ser Asp Ser Val Gln Trp Phe His Asn Gly Asn Leu Ile Pro Thr Gln
65                  70                  75                  80

Thr Gln Pro Thr Tyr Arg Phe Lys Ala Thr Ser Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Thr Pro Arg Leu Glu Phe
        115                 120                 125

Gln Glu Gly Glu Thr Ile Met Leu Arg Cys His Ser Trp Lys Asp Lys
    130                 135                 140

Pro Leu Val Lys Val Thr Phe Phe Gln Asn Gly Lys Ser Gln Lys Phe
145                 150                 155                 160

Ser His Leu Asp Pro Thr Phe Ser Ile Pro Gln Ala Asn His Ser His
                165                 170                 175

Ser Gly Asp Tyr His Cys Thr Gly Asn Ile Gly Tyr Thr Ser Phe Ser
            180                 185                 190

Ser Lys Pro Val Thr Ile Thr Val Gln Gly Gly His His His His His
        195                 200                 205

His
```

<210> SEQ ID NO 12
<211> LENGTH: 630
<212> TYPE: DNA
<213> ORGANISM: Artificial Sequence
<220> FEATURE:
<223> OTHER INFORMATION: DNA encoding MalE signal - FcgRIIa-m8B (Q69L) - 6His

<400> SEQUENCE: 12

```
atgaaaataa aaacaggtgc acgcatcctc gcattatccg cattaacgac gatgatgttt     60

tccgcctcgg ctctcgccat gggacaagcc gcagcgcctc caaaggcggt tctgaaactg    120

gagccgccgt ggattaatgt gttgcaggaa gatagcgtga cgctgacctg ccagggagcc    180

cgtagcccgg aatcagacag cgtactgtgg tttcacaacg gcaatttgat ccccactcaa    240

acgcagccga cgtaccgttt caaagccacc agtaacgatt cgggcgaata tacctgccag    300

acaggccaga ccagcctgtc ggatccagtg cacctgaccg tgctgtcaga atggctggtg    360

ctgcaaaccc cgcgtctgga atttcaggaa ggcgaaacca taatgctgcg ttgccacagc    420

tggaaagata aaccgctggt gaaggtcacg ttcttccaga acgggaagag ccagaagttc    480

tcccatctcg acccgacttt tagcatcccc caggcgaatc atagccatag cggcgattat    540

cactgcaccg ggaatattgg gtatacgtct tttagcagca agccggttac tatcaccgtg    600

cagggcggcc atcatcatca tcatcattaa                                     630
```

<210> SEQ ID NO 13
<211> LENGTH: 209
<212> TYPE: PRT
<213> ORGANISM: Artificial Sequence
<220> FEATURE:
<223> OTHER INFORMATION: MalE signal - FcRIIa-m8B (Q69L) - 6His

<400> SEQUENCE: 13

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Ile Asn Val Leu
        35                  40                  45

Gln Glu Asp Ser Val Thr Leu Thr Cys Gln Gly Ala Arg Ser Pro Glu
    50                  55                  60

Ser Asp Ser Val Leu Trp Phe His Asn Gly Asn Leu Ile Pro Thr Gln
65                  70                  75                  80

Thr Gln Pro Thr Tyr Arg Phe Lys Ala Thr Ser Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Thr Pro Arg Leu Glu Phe
        115                 120                 125

Gln Glu Gly Glu Thr Ile Met Leu Arg Cys His Ser Trp Lys Asp Lys
    130                 135                 140

Pro Leu Val Lys Val Thr Phe Phe Gln Asn Gly Lys Ser Gln Lys Phe
145                 150                 155                 160

Ser His Leu Asp Pro Thr Phe Ser Ile Pro Gln Ala Asn His Ser His
                165                 170                 175

Ser Gly Asp Tyr His Cys Thr Gly Asn Ile Gly Tyr Thr Ser Phe Ser
            180                 185                 190

Ser Lys Pro Val Thr Ile Thr Val Gln Gly Gly His His His His His
        195                 200                 205

His
```

<210> SEQ ID NO 14
<211> LENGTH: 630
<212> TYPE: DNA
<213> ORGANISM: Artificial Sequence
<220> FEATURE:
<223> OTHER INFORMATION: DNA encoding MalE signal - FcgRIIa-m8C (P83L) - 6His

<400> SEQUENCE: 14

```
atgaaaataa aaacaggtgc acgcatcctc gcattatccg cattaacgac gatgatgttt      60

tccgcctcgg ctctcgccat gggacaagcc gcagcgcctc caaaggcggt tctgaaactg     120

gagccgccgt ggattaatgt gttgcaggaa gatagcgtga cgctgacctg ccagggagcc     180

cgtagcccgg aatcagacag cgtacagtgg tttcacaacg gcaatttgat ccccactcaa     240

acgcagctga cgtaccgttt caaagccacc agtaacgatt cgggcgaata tacctgccag     300

acaggccaga ccagcctgtc ggatccagtg cacctgaccg tgctgtcaga atggctggtg     360

ctgcaaaccc cgcgtctgga atttcaggaa ggcgaaacca taatgctgcg ttgccacagc     420

tggaaagata aaccgctggt gaaggtcacg ttcttccaga acgggaagag ccagaagttc     480

tcccatctcg acccgacttt tagcatcccc caggcgaatc atagccatag cggcgattat     540

cactgcaccg ggaatattgg gtatacgtct tttagcagca agccggttac tatcaccgtg     600

cagggcggcc atcatcatca tcatcattaa                                      630
```

<210> SEQ ID NO 15
<211> LENGTH: 209

<212> TYPE: PRT
<213> ORGANISM: Artificial Sequence
<220> FEATURE:
<223> OTHER INFORMATION: MalE signal - FcgRIIa-m8C (P83L) - 6His

<400> SEQUENCE: 15

Met Lys Ile Lys Thr Gly Ala Arg Ile Leu Ala Leu Ser Ala Leu Thr
1 5 10 15

Thr Met Met Phe Ser Ala Ser Ala Leu Ala Met Gly Gln Ala Ala Ala
20 25 30

Pro Pro Lys Ala Val Leu Lys Leu Glu Pro Pro Trp Ile Asn Val Leu
35 40 45

Gln Glu Asp Ser Val Thr Leu Thr Cys Gln Gly Ala Arg Ser Pro Glu
50 55 60

Ser Asp Ser Val Gln Trp Phe His Asn Gly Asn Leu Ile Pro Thr Gln
65 70 75 80

Thr Gln Leu Thr Tyr Arg Phe Lys Ala Thr Ser Asn Asp Ser Gly Glu
85 90 95

Tyr Thr Cys Gln Thr Gly Gln Thr Ser Leu Ser Asp Pro Val His Leu
100 105 110

Thr Val Leu Ser Glu Trp Leu Val Leu Gln Thr Pro Arg Leu Glu Phe
115 120 125

Gln Glu Gly Glu Thr Ile Met Leu Arg Cys His Ser Trp Lys Asp Lys
130 135 140

Pro Leu Val Lys Val Thr Phe Phe Gln Asn Gly Lys Ser Gln Lys Phe
145 150 155 160

Ser His Leu Asp Pro Thr Phe Ser Ile Pro Gln Ala Asn His Ser His
165 170 175

Ser Gly Asp Tyr His Cys Thr Gly Asn Ile Gly Tyr Thr Ser Phe Ser
180 185 190

Ser Lys Pro Val Thr Ile Thr Val Gln Gly Gly His His His His His
195 200 205

His

<210> SEQ ID NO 16
<211> LENGTH: 630
<212> TYPE: DNA
<213> ORGANISM: Artificial Sequence
<220> FEATURE:
<223> OTHER INFORMATION: DNA encoding MalE signal - FcgRIIa-m8D (T123P) - 6His

<400> SEQUENCE: 16
atgaaaataa aaacaggtgc acgcatcctc gcattatccg cattaacgac gatgatgttt 60
tccgcctcgg ctctcgccat gggacaagcc gcagcgcctc caaaggcggt tctgaaactg 120
gagccgccgt ggattaatgt gttgcaggaa gatagcgtga cgctgacctg ccagggagcc 180
cgtagcccgg aatcagacag cgtacagtgg tttcacaacg gcaatttgat ccccactcaa 240
acgcagccga cgtaccgttt caaagccacc agtaacgatt cgggcgaata tacctgccag 300
acaggccaga ccagcctgtc ggatccagtg cacctgaccg tgctgtcaga atggctggtg 360
ctgcaaccgc cgcgtctgga atttcaggaa ggcgaaacca taatgctgcg ttgccacagc 420
tggaaagata aaccgctggt gaaggtcacg ttcttccaga acgggaagag ccagaagttc 480
tcccatctcg acccgacttt tagcatcccc caggcgaatc atagccatag cggcgattat 540
cactgcaccg ggaatattgg gtatacgtct tttagcagca agccggttac tatcaccgtg 600
cagggcggcc atcatcatca tcatcattaa 630

<210> SEQ ID NO 17
<211> LENGTH: 209
<212> TYPE: PRT
<213> ORGANISM: Artificial Sequence
<220> FEATURE:
<223> OTHER INFORMATION: MalE signal - FcRIIa-m8D (T123P) - 6His

<400> SEQUENCE: 17

Met Lys Ile Lys Thr Gly Ala Arg Ile Leu Ala Leu Ser Ala Leu Thr
1 5 10 15

Thr Met Met Phe Ser Ala Ser Ala Leu Ala Met Gly Gln Ala Ala Ala
20 25 30

Pro Pro Lys Ala Val Leu Lys Leu Glu Pro Pro Trp Ile Asn Val Leu
35 40 45

Gln Glu Asp Ser Val Thr Leu Thr Cys Gln Gly Ala Arg Ser Pro Glu
50 55 60

Ser Asp Ser Val Gln Trp Phe His Asn Gly Asn Leu Ile Pro Thr Gln
65 70 75 80

Thr Gln Pro Thr Tyr Arg Phe Lys Ala Thr Ser Asn Asp Ser Gly Glu
85 90 95

Tyr Thr Cys Gln Thr Gly Gln Thr Ser Leu Ser Asp Pro Val His Leu
100 105 110

Thr Val Leu Ser Glu Trp Leu Val Leu Gln Pro Pro Arg Leu Glu Phe
115 120 125

Gln Glu Gly Glu Thr Ile Met Leu Arg Cys His Ser Trp Lys Asp Lys
130 135 140

Pro Leu Val Lys Val Thr Phe Phe Gln Asn Gly Lys Ser Gln Lys Phe
145 150 155 160

Ser His Leu Asp Pro Thr Phe Ser Ile Pro Gln Ala Asn His Ser His
165 170 175

Ser Gly Asp Tyr His Cys Thr Gly Asn Ile Gly Tyr Thr Ser Phe Ser
180 185 190

Ser Lys Pro Val Thr Ile Thr Val Gln Gly Gly His His His His His
195 200 205

His

<210> SEQ ID NO 18
<211> LENGTH: 630
<212> TYPE: DNA
<213> ORGANISM: Artificial Sequence
<220> FEATURE:
<223> OTHER INFORMATION: DNA encoding MalE signal - FcRIIa-m10A (I45T, Q69L) - 6His

<400> SEQUENCE: 18
atgaaaataa aaacaggtgc acgcatcctc gcattatccg cattaacgac gatgatgttt 60
tccgcctcgg ctctcgccat gggacaagcc gcagcgcctc caaaggcggt tctgaaactg 120
gagccgccgt ggaccaatgt gttgcaggaa gatagcgtga cgctgacctg ccagggagcc 180
cgtagcccgg aatcagacag cgtactgtgg tttcacaacg gcaatttgat ccccactcaa 240
acgcagccga cgtaccgttt caaagccacc agtaacgatt cgggcgaata tacctgccag 300
acaggccaga ccagcctgtc ggatccagtg cacctgaccg tgctgtcaga atggctggtg 360

```
ctgcaaccgc cgcgtctgga atttcaggaa ggcgaaacca taatgctgcg ttgccacagc    420

tggaaagata aaccgctggt gaaggtcacg ttcttccaga acgggaagag ccagaagttc    480

tcccatctcg acccgacttt tagcatcccc caggcgaatc atagccatag cggcgattat    540

cactgcaccg ggaatattgg gtatacgtct tttagcagca agccggttac tatcaccgtg    600

cagggcggcc atcatcatca tcatcattaa                                     630


<210> SEQ ID NO 19
<211> LENGTH: 209
<212> TYPE: PRT
<213> ORGANISM: Artificial Sequence
<220> FEATURE:
<223> OTHER INFORMATION: MalE signal - FcRIIa-m10A (I45T, Q69L) - 6His

<400> SEQUENCE: 19

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Thr Asn Val Leu
        35                  40                  45

Gln Glu Asp Ser Val Thr Leu Thr Cys Gln Gly Ala Arg Ser Pro Glu
    50                  55                  60

Ser Asp Ser Val Leu Trp Phe His Asn Gly Asn Leu Ile Pro Thr Gln
65                  70                  75                  80

Thr Gln Pro Thr Tyr Arg Phe Lys Ala Thr Ser Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Pro Pro Arg Leu Glu Phe
        115                 120                 125

Gln Glu Gly Glu Thr Ile Met Leu Arg Cys His Ser Trp Lys Asp Lys
    130                 135                 140

Pro Leu Val Lys Val Thr Phe Phe Gln Asn Gly Lys Ser Gln Lys Phe
145                 150                 155                 160

Ser His Leu Asp Pro Thr Phe Ser Ile Pro Gln Ala Asn His Ser His
                165                 170                 175

Ser Gly Asp Tyr His Cys Thr Gly Asn Ile Gly Tyr Thr Ser Phe Ser
            180                 185                 190

Ser Lys Pro Val Thr Ile Thr Val Gln Gly Gly His His His His His
        195                 200                 205

His


<210> SEQ ID NO 20
<211> LENGTH: 630
<212> TYPE: DNA
<213> ORGANISM: Artificial Sequence
<220> FEATURE:
<223> OTHER INFORMATION: DNA encoding MalE signal - FcgRIIa-m10B (I45T,
      P83L) - 6His

<400> SEQUENCE: 20

atgaaaataa aaacaggtgc acgcatcctc gcattatccg cattaacgac gatgatgttt     60

tccgcctcgg ctctcgccat gggacaagcc gcagcgcctc caaaggcggt tctgaaactg    120

gagccgccgt ggaccaatgt gttgcaggaa gatagcgtga cgctgacctg ccagggagcc    180

cgtagcccgg aatcagacag cgtacagtgg tttcacaacg gcaatttgat ccccactcaa    240
```

```
acgcagctga cgtaccgttt caaagccacc agtaacgatt cgggcgaata tacctgccag    300

acaggccaga ccagcctgtc ggatccagtg cacctgaccg tgctgtcaga atggctggtg    360

ctgcaaccgc cgcgtctgga atttcaggaa ggcgaaacca taatgctgcg ttgccacagc    420

tggaaagata aaccgctggt gaaggtcacg ttcttccaga acgggaagag ccagaagttc    480

tcccatctcg acccgacttt tagcatcccc caggcgaatc atagccatag cggcgattat    540

cactgcaccg ggaatattgg gtatacgtct tttagcagca agccggttac tatcaccgtg    600

cagggcggcc atcatcatca tcatcattaa                                     630
```

<210> SEQ ID NO 21
<211> LENGTH: 209
<212> TYPE: PRT
<213> ORGANISM: Artificial Sequence
<220> FEATURE:
<223> OTHER INFORMATION: MalE signal - FcRIIa-m10B (I45T, P83L) - 6His

<400> SEQUENCE: 21

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Thr Asn Val Leu
        35                  40                  45

Gln Glu Asp Ser Val Thr Leu Thr Cys Gln Gly Ala Arg Ser Pro Glu
    50                  55                  60

Ser Asp Ser Val Gln Trp Phe His Asn Gly Asn Leu Ile Pro Thr Gln
65                  70                  75                  80

Thr Gln Leu Thr Tyr Arg Phe Lys Ala Thr Ser Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Pro Pro Arg Leu Glu Phe
        115                 120                 125

Gln Glu Gly Glu Thr Ile Met Leu Arg Cys His Ser Trp Lys Asp Lys
    130                 135                 140

Pro Leu Val Lys Val Thr Phe Phe Gln Asn Gly Lys Ser Gln Lys Phe
145                 150                 155                 160

Ser His Leu Asp Pro Thr Phe Ser Ile Pro Gln Ala Asn His Ser His
                165                 170                 175

Ser Gly Asp Tyr His Cys Thr Gly Asn Ile Gly Tyr Thr Ser Phe Ser
            180                 185                 190

Ser Lys Pro Val Thr Ile Thr Val Gln Gly Gly His His His His His
        195                 200                 205

His
```

<210> SEQ ID NO 22
<211> LENGTH: 630
<212> TYPE: DNA
<213> ORGANISM: Artificial Sequence
<220> FEATURE:
<223> OTHER INFORMATION: DNA encoding MalE signal - FcgRIIa-m10C (Q69L, P83L) - 6His

<400> SEQUENCE: 22

```
atgaaaataa aaacaggtgc acgcatcctc gcattatccg cattaacgac gatgatgttt      60

tccgcctcgg ctctcgccat gggacaagcc gcagcgcctc caaaggcggt tctgaaactg     120

gagccgccgt ggattaatgt gttgcaggaa gatagcgtga cgctgacctg ccagggagcc     180

cgtagcccgg aatcagacag cgtactgtgg tttcacaacg gcaatttgat ccccactcaa     240

acgcagctga cgtaccgttt caaagccacc agtaacgatt cgggcgaata tacctgccag     300

acaggccaga ccagcctgtc ggatccagtg cacctgaccg tgctgtcaga atggctggtg     360

ctgcaaccgc cgcgtctgga atttcaggaa ggcgaaacca taatgctgcg ttgccacagc     420

tggaaagata aaccgctggt gaaggtcacg ttcttccaga acgggaagag ccagaagttc     480

tcccatctcg acccgacttt tagcatcccc caggcgaatc atagccatag cggcgattat     540

cactgcaccg ggaatattgg gtatacgtct tttagcagca agccggttac tatcaccgtg     600

cagggcggcc atcatcatca tcatcattaa                                      630
```

<210> SEQ ID NO 23
<211> LENGTH: 209
<212> TYPE: PRT
<213> ORGANISM: Artificial Sequence
<220> FEATURE:
<223> OTHER INFORMATION: MalE signal - FcgRIIa-m10C (Q69L, P83L) - 6His

<400> SEQUENCE: 23

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Ile Asn Val Leu
        35                  40                  45

Gln Glu Asp Ser Val Thr Leu Thr Cys Gln Gly Ala Arg Ser Pro Glu
    50                  55                  60

Ser Asp Ser Val Leu Trp Phe His Asn Gly Asn Leu Ile Pro Thr Gln
65                  70                  75                  80

Thr Gln Leu Thr Tyr Arg Phe Lys Ala Thr Ser Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Pro Pro Arg Leu Glu Phe
        115                 120                 125

Gln Glu Gly Glu Thr Ile Met Leu Arg Cys His Ser Trp Lys Asp Lys
    130                 135                 140

Pro Leu Val Lys Val Thr Phe Phe Gln Asn Gly Lys Ser Gln Lys Phe
145                 150                 155                 160

Ser His Leu Asp Pro Thr Phe Ser Ile Pro Gln Ala Asn His Ser His
                165                 170                 175

Ser Gly Asp Tyr His Cys Thr Gly Asn Ile Gly Tyr Thr Ser Phe Ser
            180                 185                 190

Ser Lys Pro Val Thr Ile Thr Val Gln Gly Gly His His His His His
        195                 200                 205

His
```

<210> SEQ ID NO 24
<211> LENGTH: 630

<212> TYPE: DNA
<213> ORGANISM: Artificial Sequence
<220> FEATURE:
<223> OTHER INFORMATION: DNA encoding MalE signal - FcgRIIa-m11 - 6His

<400> SEQUENCE: 24

```
atgaaaataa aaacaggtgc acgcatcctc gcattatccg cattaacgac gatgatgttt      60

tccgcctcgg ctctcgccat gggacaagcc gcagcgcctc caaaggcggt tctgaaactg     120

gagccgccgt ggaccaatgt gttgcaggaa gatagcgtga cgctgacctg ccagggagcc     180

cgtagcccgg aatcagacag cgtactgtgg tttcacaacg gcaatttgat ccccactcaa     240

acgcagctga cgtaccgttt caaagccacc agtaacgatt cgggcgaata tacctgccag     300

acaggccaga ccagcctgtc ggatccagtg cacctgaccg tgctgtcaga atggctggtg     360

ctgcaaccgc cgcgtctgga atttcaggaa ggcgaaacca taatgctgcg ttgccacagc     420

tggaaagata aaccgctggt gaaggtcacg ttcttccaga acgggaagag ccagaagttc     480

tcccatctcg acccgacttt tagcatcccc caggcgaatc atagccatag cggcgattat     540

cactgcaccg ggaatattgg gtatacgtct tttagcagca agccggttac tatcaccgtg     600

cagggcggcc atcatcatca tcatcattaa                                      630
```

<210> SEQ ID NO 25
<211> LENGTH: 209
<212> TYPE: PRT
<213> ORGANISM: Artificial Sequence
<220> FEATURE:
<223> OTHER INFORMATION: MalE signal - FcgRIIa-m11 - 6His

<400> SEQUENCE: 25

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Thr Asn Val Leu
        35                  40                  45

Gln Glu Asp Ser Val Thr Leu Thr Cys Gln Gly Ala Arg Ser Pro Glu
    50                  55                  60

Ser Asp Ser Val Leu Trp Phe His Asn Gly Asn Leu Ile Pro Thr Gln
65                  70                  75                  80

Thr Gln Leu Thr Tyr Arg Phe Lys Ala Thr Ser Asn Asp Ser Gly Glu
                85                  90                  95

Tyr Thr Cys Gln Thr Gly Gln Thr Ser Leu Ser Asp Pro Val His Leu
            100                 105                 110

Thr Val Leu Ser Glu Trp Leu Val Leu Gln Pro Pro Arg Leu Glu Phe
        115                 120                 125

Gln Glu Gly Glu Thr Ile Met Leu Arg Cys His Ser Trp Lys Asp Lys
    130                 135                 140

Pro Leu Val Lys Val Thr Phe Phe Gln Asn Gly Lys Ser Gln Lys Phe
145                 150                 155                 160

Ser His Leu Asp Pro Thr Phe Ser Ile Pro Gln Ala Asn His Ser His
                165                 170                 175

Ser Gly Asp Tyr His Cys Thr Gly Asn Ile Gly Tyr Thr Ser Phe Ser
            180                 185                 190

Ser Lys Pro Val Thr Ile Thr Val Gln Gly Gly His His His His His
        195                 200                 205

His
```

<210> SEQ ID NO 26
<211> LENGTH: 34
<212> TYPE: DNA
<213> ORGANISM: Artificial Sequence
<220> FEATURE:
<223> OTHER INFORMATION: Oligonucleotide I45T - F

<400> SEQUENCE: 26
ctggagccgc cgtggaccaa tgtgttgcag gaag 34

<210> SEQ ID NO 27
<211> LENGTH: 33
<212> TYPE: DNA
<213> ORGANISM: Artificial Sequence
<220> FEATURE:
<223> OTHER INFORMATION: Oligonucleotide I45T - R

<400> SEQUENCE: 27
ttcctgcaac acattggtcc acggcggctc cag 33

<210> SEQ ID NO 28
<211> LENGTH: 33
<212> TYPE: DNA
<213> ORGANISM: Artificial Sequence
<220> FEATURE:
<223> OTHER INFORMATION: Oligonucleotide Q69L - F

<400> SEQUENCE: 28
gaatcagaca gcgtactgtg gtttcacaac ggc 33

<210> SEQ ID NO 29
<211> LENGTH: 33
<212> TYPE: DNA
<213> ORGANISM: Artificial Sequence
<220> FEATURE:
<223> OTHER INFORMATION: Oligonucleotide Q69L - R

<400> SEQUENCE: 29
gccgttgtga aaccagacta cgctgtctga ttc 33

<210> SEQ ID NO 30
<211> LENGTH: 36
<212> TYPE: DNA
<213> ORGANISM: Artificial Sequence
<220> FEATURE:
<223> OTHER INFORMATION: Oligonucleotide P83L - F

<400> SEQUENCE: 30
actcaaacgc agctgacgta ccgtttcaaa gccacc 36

<210> SEQ ID NO 31
<211> LENGTH: 37
<212> TYPE: DNA
<213> ORGANISM: Artificial Sequence
<220> FEATURE:
<223> OTHER INFORMATION: Oligonucleotide P83L - R

<400> SEQUENCE: 31
tttgaaacgg tacgtcagct gcgtttgagt ggggatc 37

<210> SEQ ID NO 32
<211> LENGTH: 34
<212> TYPE: DNA
<213> ORGANISM: Artificial Sequence
<220> FEATURE:

<223> OTHER INFORMATION: Oligonucleotide T123P - F

<400> SEQUENCE: 32
tggctggtgc tgcaaccgcc gcgtctggaa tttc 34

<210> SEQ ID NO 33
<211> LENGTH: 32
<212> TYPE: DNA
<213> ORGANISM: Artificial Sequence
<220> FEATURE:
<223> OTHER INFORMATION: Oligonucleotide T123P - R

<400> SEQUENCE: 33
aaattccaga cgcggcggtt gcagcaccag cc 32

<210> SEQ ID NO 34
<211> LENGTH: 628
<212> TYPE: DNA
<213> ORGANISM: Homo sapiens
<220> FEATURE:
<223> OTHER INFORMATION: DNA encoding MalE signal - FcgRIIa(m11)-Del1 - 6His

<400> SEQUENCE: 34
atgaaaataa aaacaggtgc acgcatcctc gcattatccg cattaacgac gatgatgttt 60
tccgcctcgg ctctcgccat gggacaagcc gcagcgcctc caaaggcggt tctgaaactg 120
gagccgccgt ggaccaatgt gttgcaggaa gatagcgtga cgctgacctg ccagggagcc 180
cgtccggaat cagacagcgt actgtggttt cacaacggca atttgatccc cactcaaacg 240
cagctgacgt accgtttcaa agccaccagt aacgattcgg gcgaatatac ctgccagaca 300
ggccagacca gcctgtcgga tccagtgcac ctgaccgtgc tgtcagaatg gctggtgctg 360
caaccgccgc gtctggaatt tcaggaaggc gaaaccataa tgctgcgttg ccacagctgg 420
aaagataaac cgctggtgaa ggtcacgttc ttccagaacg ggaagagcca gaagttctcc 480
catctcgacc cgacttttag catcccccag gcgaatcata gccatagcgg cgattatcac 540
tgcaccggga atattgggta tacgtctttt agcagcaagc cggttactat caccgtgcag 600
ggcggccatc atcatcatca tcattaag 628

<210> SEQ ID NO 35
<211> LENGTH: 208
<212> TYPE: PRT
<213> ORGANISM: Homo sapiens
<220> FEATURE:
<223> OTHER INFORMATION: MalE signal - FcgRIIa(m11)-Del1 - 6His

<400> SEQUENCE: 35

Met Lys Ile Lys Thr Gly Ala Arg Ile Leu Ala Leu Ser Ala Leu Thr
1 5 10 15

Thr Met Met Phe Ser Ala Ser Ala Leu Ala Met Gly Gln Ala Ala Ala
20 25 30

Pro Pro Lys Ala Val Leu Lys Leu Glu Pro Pro Trp Thr Asn Val Leu
35 40 45

Gln Glu Asp Ser Val Thr Leu Thr Cys Gln Gly Ala Arg Pro Glu Ser
50 55 60

Asp Ser Val Leu Trp Phe His Asn Gly Asn Leu Ile Pro Thr Gln Thr
65 70 75 80

Gln Leu Thr Tyr Arg Phe Lys Ala Thr Ser Asn Asp Ser Gly Glu Tyr
85 90 95

```
Thr Cys Gln Thr Gly Gln Thr Ser Leu Ser Asp Pro Val His Leu Thr
            100                 105                 110

Val Leu Ser Glu Trp Leu Val Leu Gln Pro Pro Arg Leu Glu Phe Gln
        115                 120                 125

Glu Gly Glu Thr Ile Met Leu Arg Cys His Ser Trp Lys Asp Lys Pro
    130                 135                 140

Leu Val Lys Val Thr Phe Phe Gln Asn Gly Lys Ser Gln Lys Phe Ser
145                 150                 155                 160

His Leu Asp Pro Thr Phe Ser Ile Pro Gln Ala Asn His Ser His Ser
                165                 170                 175

Gly Asp Tyr His Cys Thr Gly Asn Ile Gly Tyr Thr Ser Phe Ser Ser
            180                 185                 190

Lys Pro Val Thr Ile Thr Val Gln Gly Gly His His His His His His
        195                 200                 205


<210> SEQ ID NO 36
<211> LENGTH: 625
<212> TYPE: DNA
<213> ORGANISM: Homo sapiens
<220> FEATURE:
<223> OTHER INFORMATION: DNA encoding MalE signal - FcgRIIa(m11)-Del2 -
      6His

<400> SEQUENCE: 36

atgaaaataa aaacaggtgc acgcatcctc gcattatccg cattaacgac gatgatgttt      60

tccgcctcgg ctctcgccat gggaactccc gcagcgcctc caaaggcggt tctgaaactg     120

gagccgcagt ggaccaatgt gttgcaggaa gatagcgtga cgctgacctg ccgtggaacc     180

catccgtcag acagcgtact gtggtttcac aacggcaatt tgatccccac tcaaacgcag     240

ctgacgtacc gtttcaaagc caccagtaac gattcgggcg aatatacctg ccagacaggc     300

cagaccagcc tgtcggatcc agtgcacctg accgtgctgt cagaatggct ggtgctgcaa     360

ccgccgcgtc tggaatttca ggaaggcgaa accatagtgc tgcgttgcca cagctggaaa     420

gataaaccgc tggtgaaggt cacgttcttc cagaacggga agagcaagaa gttctcccgt     480

agcgacccga attttagcat cccccaggcg aatcatagcc atagcggcga ttatcactgc     540

accgggaata ttgggtatac gtcttatagc agcaagccgg ttactatcac cgtgcagggc     600

ggccatcatc atcatcatca ttaag                                           625


<210> SEQ ID NO 37
<211> LENGTH: 207
<212> TYPE: PRT
<213> ORGANISM: Homo sapiens
<220> FEATURE:
<223> OTHER INFORMATION: MalE signal - FcgRIIa(m11)-Del2 - 6His

<400> SEQUENCE: 37

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Thr Asn Val Leu
        35                  40                  45

Gln Glu Asp Ser Val Thr Leu Thr Cys Gln Gly Ala Arg Pro Ser Asp
    50                  55                  60

Ser Val Leu Trp Phe His Asn Gly Asn Leu Ile Pro Thr Gln Thr Gln
65                  70                  75                  80
```

```
Leu Thr Tyr Arg Phe Lys Ala Thr Ser Asn Asp Ser Gly Glu Tyr Thr
                85                  90                  95

Cys Gln Thr Gly Gln Thr Ser Leu Ser Asp Pro Val His Leu Thr Val
            100                 105                 110

Leu Ser Glu Trp Leu Val Leu Gln Pro Pro Arg Leu Glu Phe Gln Glu
        115                 120                 125

Gly Glu Thr Ile Met Leu Arg Cys His Ser Trp Lys Asp Lys Pro Leu
    130                 135                 140

Val Lys Val Thr Phe Phe Gln Asn Gly Lys Ser Gln Lys Phe Ser His
145                 150                 155                 160

Leu Asp Pro Thr Phe Ser Ile Pro Gln Ala Asn His Ser His Ser Gly
                165                 170                 175

Asp Tyr His Cys Thr Gly Asn Ile Gly Tyr Thr Ser Phe Ser Ser Lys
            180                 185                 190

Pro Val Thr Ile Thr Val Gln Gly Gly His His His His His His
        195                 200                 205


<210> SEQ ID NO 38
<211> LENGTH: 622
<212> TYPE: DNA
<213> ORGANISM: Homo sapiens
<220> FEATURE:
<223> OTHER INFORMATION: DNA encoding MalE signal - FcgRIIa(m11)-Del3 -
      6His

<400> SEQUENCE: 38

atgaaaataa aaacaggtgc acgcatcctc gcattatccg cattaacgac gatgatgttt     60

tccgcctcgg ctctcgccat gggacaagcc gcagcgcctc caaaggcggt tctgaaactg    120

gagccgccgt ggaccaatgt gttgcaggaa gatagcgtga cgctgacctg ccagggagcc    180

cgttcagaca gcgtactgtg gtttcacaac ggcaatttga tccccactca aacgcagctg    240

acgtaccgtt tcaaagccac cagtaacgat tcgggcgaat atacctgcca gacaggccag    300

accagcctgt cggatccagt gcacctgacc gtgctgtcag aatggctggt gctgcaaccg    360

ccgcgtctgg aatttcagga aggcgaaacc ataatgctgc gttgccacag ctggaaagat    420

aaaccgctgg tgaaggtcac gttcttccag aacgggaaga gccagaagtt ctcccatctc    480

gacccgactt ttagcatccc ccaggcgaat catagccata gcggcgatta tcactgcacc    540

gggaatattg ggtatacgtc ttttagcagc aagccggtta ctatcaccgt gcagggcggc    600

catcatcatc atcatcatta ag                                             622


<210> SEQ ID NO 39
<211> LENGTH: 206
<212> TYPE: PRT
<213> ORGANISM: Homo sapiens
<220> FEATURE:
<223> OTHER INFORMATION: MalE signal - FcgRIIa(m11)-Del3 - 6His

<400> SEQUENCE: 39

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Thr Asn Val Leu
        35                  40                  45

Gln Glu Asp Ser Val Thr Leu Thr Cys Gln Gly Ala Arg Ser Asp Ser
    50                  55                  60
```

Val Leu Trp Phe His Asn Gly Asn Leu Ile Pro Thr Gln Thr Gln Leu
65 70 75 80

Thr Tyr Arg Phe Lys Ala Thr Ser Asn Asp Ser Gly Glu Tyr Thr Cys
85 90 95

Gln Thr Gly Gln Thr Ser Leu Ser Asp Pro Val His Leu Thr Val Leu
100 105 110

Ser Glu Trp Leu Val Leu Gln Pro Pro Arg Leu Glu Phe Gln Glu Gly
115 120 125

Glu Thr Ile Met Leu Arg Cys His Ser Trp Lys Asp Lys Pro Leu Val
130 135 140

Lys Val Thr Phe Phe Gln Asn Gly Lys Ser Gln Lys Phe Ser His Leu
145 150 155 160

Asp Pro Thr Phe Ser Ile Pro Gln Ala Asn His Ser His Ser Gly Asp
165 170 175

Tyr His Cys Thr Gly Asn Ile Gly Tyr Thr Ser Phe Ser Ser Lys Pro
180 185 190

Val Thr Ile Thr Val Gln Gly Gly His His His His His His
195 200 205

<210> SEQ ID NO 40
<211> LENGTH: 619
<212> TYPE: DNA
<213> ORGANISM: Homo sapiens
<220> FEATURE:
<223> OTHER INFORMATION: DNA encoding MalE signal - FcgRIIa(m11)-Del4 - 6His

<400> SEQUENCE: 40
atgaaaataa aaacaggtgc acgcatcctc gcattatccg cattaacgac gatgatgttt 60
tccgcctcgg ctctcgccat gggacaagcc gcagcgcctc caaaggcggt tctgaaactg 120
gagccgccgt ggaccaatgt gttgcaggaa gatagcgtga cgctgacctg ccagggagcc 180
tcagacagcg tactgtggtt tcacaacggc aatttgatcc ccactcaaac gcagctgacg 240
taccgtttca aagccaccag taacgattcg ggcgaatata cctgccagac aggccagacc 300
agcctgtcgg atccagtgca cctgaccgtg ctgtcagaat ggctggtgct gcaaccgccg 360
cgtctggaat ttcaggaagg cgaaaccata atgctgcgtt gccacagctg gaaagataaa 420
ccgctggtga aggtcacgtt cttccagaac gggaagagcc agaagttctc ccatctcgac 480
ccgactttta gcatccccca ggcgaatcat agccatagcg gcgattatca ctgcaccggg 540
aatattgggt atacgtcttt tagcagcaag ccggttacta tcaccgtgca gggcggccat 600
catcatcatc atcattaag 619

<210> SEQ ID NO 41
<211> LENGTH: 205
<212> TYPE: PRT
<213> ORGANISM: Homo sapiens
<220> FEATURE:
<223> OTHER INFORMATION: MalE signal - FcgRIIa(m11)-Del4 - 6His

<400> SEQUENCE: 41

Met Lys Ile Lys Thr Gly Ala Arg Ile Leu Ala Leu Ser Ala Leu Thr
1 5 10 15

Thr Met Met Phe Ser Ala Ser Ala Leu Ala Met Gly Gln Ala Ala Ala
20 25 30

Pro Pro Lys Ala Val Leu Lys Leu Glu Pro Pro Trp Thr Asn Val Leu
35 40 45

```
Gln Glu Asp Ser Val Thr Leu Thr Cys Gln Gly Ala Ser Asp Ser Val
    50                  55                  60

Leu Trp Phe His Asn Gly Asn Leu Ile Pro Thr Gln Thr Gln Leu Thr
65                  70                  75                  80

Tyr Arg Phe Lys Ala Thr Ser Asn Asp Ser Gly Glu Tyr Thr Cys Gln
                85                  90                  95

Thr Gly Gln Thr Ser Leu Ser Asp Pro Val His Leu Thr Val Leu Ser
            100                 105                 110

Glu Trp Leu Val Leu Gln Pro Pro Arg Leu Glu Phe Gln Glu Gly Glu
        115                 120                 125

Thr Ile Met Leu Arg Cys His Ser Trp Lys Asp Lys Pro Leu Val Lys
    130                 135                 140

Val Thr Phe Phe Gln Asn Gly Lys Ser Gln Lys Phe Ser His Leu Asp
145                 150                 155                 160

Pro Thr Phe Ser Ile Pro Gln Ala Asn His Ser His Ser Gly Asp Tyr
                165                 170                 175

His Cys Thr Gly Asn Ile Gly Tyr Thr Ser Phe Ser Ser Lys Pro Val
            180                 185                 190

Thr Ile Thr Val Gln Gly Gly His His His His His His
        195                 200                 205
```

<210> SEQ ID NO 42
<211> LENGTH: 616
<212> TYPE: DNA
<213> ORGANISM: Homo sapiens
<220> FEATURE:
<223> OTHER INFORMATION: DNA encoding MalE signal - FcgRIIa(m11)-Del5 - 6His

<400> SEQUENCE: 42

```
atgaaaataa aaacaggtgc acgcatcctc gcattatccg cattaacgac gatgatgttt      60

tccgcctcgg ctctcgccat gggacaagcc gcagcgcctc caaaggcggt tctgaaactg     120

gagccgccgt ggaccaatgt gttgcaggaa gatagcgtga cgctgacctg ccagggagcc     180

gacagcgtac tgtggtttca caacggcaat ttgatcccca ctcaaacgca gctgacgtac     240

cgtttcaaag ccaccagtaa cgattcgggc gaatatacct gccagacagg ccagaccagc     300

ctgtcggatc cagtgcacct gaccgtgctg tcagaatggc tggtgctgca accgccgcgt     360

ctggaatttc aggaaggcga aaccataatg ctgcgttgcc acagctggaa agataaaccg     420

ctggtgaagg tcacgttctt ccagaacggg aagagccaga agttctccca tctcgacccg     480

acttttagca tcccccaggc gaatcatagc catagcggcg attatcactg caccgggaat     540

attgggtata cgtcttttag cagcaagccg gttactatca ccgtgcaggg cggccatcat     600

catcatcatc attaag                                                     616
```

<210> SEQ ID NO 43
<211> LENGTH: 204
<212> TYPE: PRT
<213> ORGANISM: Homo sapiens
<220> FEATURE:
<223> OTHER INFORMATION: MalE signal - FcgRIIa(m11)-Del5 - 6His

<400> SEQUENCE: 43

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30
```

```
Pro Pro Lys Ala Val Leu Lys Leu Glu Pro Pro Trp Thr Asn Val Leu
        35                  40                  45

Gln Glu Asp Ser Val Thr Leu Thr Cys Gln Gly Ala Asp Ser Val Leu
    50                  55                  60

Trp Phe His Asn Gly Asn Leu Ile Pro Thr Gln Thr Gln Leu Thr Tyr
65                  70                  75                  80

Arg Phe Lys Ala Thr Ser Asn Asp Ser Gly Glu Tyr Thr Cys Gln Thr
                85                  90                  95

Gly Gln Thr Ser Leu Ser Asp Pro Val His Leu Thr Val Leu Ser Glu
            100                 105                 110

Trp Leu Val Leu Gln Pro Pro Arg Leu Glu Phe Gln Glu Gly Glu Thr
        115                 120                 125

Ile Met Leu Arg Cys His Ser Trp Lys Asp Lys Pro Leu Val Lys Val
    130                 135                 140

Thr Phe Phe Gln Asn Gly Lys Ser Gln Lys Phe Ser His Leu Asp Pro
145                 150                 155                 160

Thr Phe Ser Ile Pro Gln Ala Asn His Ser His Ser Gly Asp Tyr His
                165                 170                 175

Cys Thr Gly Asn Ile Gly Tyr Thr Ser Phe Ser Ser Lys Pro Val Thr
            180                 185                 190

Ile Thr Val Gln Gly Gly His His His His His His
        195                 200
```

<210> SEQ ID NO 44
<211> LENGTH: 613
<212> TYPE: DNA
<213> ORGANISM: Homo sapiens
<220> FEATURE:
<223> OTHER INFORMATION: DNA encoding MalE signal - FcgRIIa(m11)-Del6 - 6His

<400> SEQUENCE: 44

```
atgaaaataa aaacaggtgc acgcatcctc gcattatccg cattaacgac gatgatgttt      60

tccgcctcgg ctctcgccat gggacaagcc gcagcgcctc caaaggcggt tctgaaactg     120

gagccgccgt ggaccaatgt gttgcaggaa gatagcgtga cgctgacctg ccagggagac     180

agcgtactgt ggtttcacaa cggcaatttg atccccactc aaacgcagct gacgtaccgt     240

ttcaaagcca ccagtaacga ttcgggcgaa tatacctgcc agacaggcca gaccagcctg     300

tcggatccag tgcacctgac cgtgctgtca gaatggctgg tgctgcaacc gccgcgtctg     360

gaatttcagg aaggcgaaac cataatgctg cgttgccaca gctggaaaga taaaccgctg     420

gtgaaggtca cgttcttcca gaacgggaag agccagaagt tctcccatct cgacccgact     480

tttagcatcc cccaggcgaa tcatagccat agcggcgatt atcactgcac cgggaatatt     540

gggtatacgt cttttagcag caagccggtt actatcaccg tgcagggcgg ccatcatcat     600

catcatcatt aag                                                        613
```

<210> SEQ ID NO 45
<211> LENGTH: 203
<212> TYPE: PRT
<213> ORGANISM: Homo sapiens
<220> FEATURE:
<223> OTHER INFORMATION: MalE signal - FcgRIIa(m11)-Del6 - 6His

<400> SEQUENCE: 45

```
Met Lys Ile Lys Thr Gly Ala Arg Ile Leu Ala Leu Ser Ala Leu Thr
1               5                   10                  15
```

```
Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Thr Asn Val Leu
        35                  40                  45

Gln Glu Asp Ser Val Thr Leu Thr Cys Gln Gly Asp Ser Val Leu Trp
    50                  55                  60

Phe His Asn Gly Asn Leu Ile Pro Thr Gln Thr Gln Leu Thr Tyr Arg
65                  70                  75                  80

Phe Lys Ala Thr Ser Asn Asp Ser Gly Glu Tyr Thr Cys Gln Thr Gly
                85                  90                  95

Gln Thr Ser Leu Ser Asp Pro Val His Leu Thr Val Leu Ser Glu Trp
            100                 105                 110

Leu Val Leu Gln Pro Pro Arg Leu Glu Phe Gln Glu Gly Glu Thr Ile
        115                 120                 125

Met Leu Arg Cys His Ser Trp Lys Asp Lys Pro Leu Val Lys Val Thr
    130                 135                 140

Phe Phe Gln Asn Gly Lys Ser Gln Lys Phe Ser His Leu Asp Pro Thr
145                 150                 155                 160

Phe Ser Ile Pro Gln Ala Asn His Ser His Ser Gly Asp Tyr His Cys
                165                 170                 175

Thr Gly Asn Ile Gly Tyr Thr Ser Phe Ser Ser Lys Pro Val Thr Ile
            180                 185                 190

Thr Val Gln Gly Gly His His His His His His
        195                 200
```

<210> SEQ ID NO 46
<211> LENGTH: 610
<212> TYPE: DNA
<213> ORGANISM: Homo sapiens
<220> FEATURE:
<223> OTHER INFORMATION: DNA encoding MalE signal - FcgRIIa(m11)-Del7 - 6His

<400> SEQUENCE: 46

```
atgaaaataa aaacaggtgc acgcatcctc gcattatccg cattaacgac gatgatgttt      60

tccgcctcgg ctctcgccat gggacaagcc gcagcgcctc caaaggcggt tctgaaactg     120

gagccgccgt ggaccaatgt gttgcaggaa gatagcgtga cgctgacctg ccaggacagc     180

gtactgtggt ttcacaacgg caatttgatc cccactcaaa cgcagctgac gtaccgtttc     240

aaagccacca gtaacgattc gggcgaatat acctgccaga caggccagac cagcctgtcg     300

gatccagtgc acctgaccgt gctgtcagaa tggctggtgc tgcaaccgcc gcgtctggaa     360

tttcaggaag gcgaaaccat aatgctgcgt tgccacagct ggaaagataa accgctggtg     420

aaggtcacgt tcttccagaa cgggaagagc cagaagttct cccatctcga cccgactttt     480

agcatccccc aggcgaatca tagccatagc ggcgattatc actgcaccgg gaatattggg     540

tatacgtctt ttagcagcaa gccggttact atcaccgtgc agggcggcca tcatcatcat     600

catcattaag                                                            610
```

<210> SEQ ID NO 47
<211> LENGTH: 202
<212> TYPE: PRT
<213> ORGANISM: Homo sapiens
<220> FEATURE:
<223> OTHER INFORMATION: MalE signal - FcgRIIa(m11)-Del7 - 6His

<400> SEQUENCE: 47

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Thr Asn Val Leu
        35                  40                  45

Gln Glu Asp Ser Val Thr Leu Thr Cys Gln Asp Ser Val Leu Trp Phe
    50                  55                  60

His Asn Gly Asn Leu Ile Pro Thr Gln Thr Gln Leu Thr Tyr Arg Phe
65                  70                  75                  80

Lys Ala Thr Ser Asn Asp Ser Gly Glu Tyr Thr Cys Gln Thr Gly Gln
                85                  90                  95

Thr Ser Leu Ser Asp Pro Val His Leu Thr Val Leu Ser Glu Trp Leu
            100                 105                 110

Val Leu Gln Pro Pro Arg Leu Glu Phe Gln Glu Gly Glu Thr Ile Met
        115                 120                 125

Leu Arg Cys His Ser Trp Lys Asp Lys Pro Leu Val Lys Val Thr Phe
    130                 135                 140

Phe Gln Asn Gly Lys Ser Gln Lys Phe Ser His Leu Asp Pro Thr Phe
145                 150                 155                 160

Ser Ile Pro Gln Ala Asn His Ser His Ser Gly Asp Tyr His Cys Thr
                165                 170                 175

Gly Asn Ile Gly Tyr Thr Ser Phe Ser Ser Lys Pro Val Thr Ile Thr
            180                 185                 190

Val Gln Gly Gly His His His His His His
        195                 200

<210> SEQ ID NO 48
<211> LENGTH: 607
<212> TYPE: DNA
<213> ORGANISM: Homo sapiens
<220> FEATURE:
<223> OTHER INFORMATION: DNA encoding MalE signal - FcgRIIa(m11)-Del8 - 6His

<400> SEQUENCE: 48
atgaaaataa aaacaggtgc acgcatcctc gcattatccg cattaacgac gatgatgttt 60
tccgcctcgg ctctcgccat gggacaagcc gcagcgcctc caaaggcggt tctgaaactg 120
gagccgccgt ggaccaatgt gttgcaggaa gatagcgtga cgctgacctg ccagagcgta 180
ctgtggtttc acaacggcaa tttgatcccc actcaaacgc agctgacgta ccgtttcaaa 240
gccaccagta acgattcggg cgaatatacc tgccagacag gccagaccag cctgtcggat 300
ccagtgcacc tgaccgtgct gtcagaatgg ctggtgctgc aaccgccgcg tctggaattt 360
caggaaggcg aaaccataat gctgcgttgc cacagctgga aagataaacc gctggtgaag 420
gtcacgttct tccagaacgg gaagagccag aagttctccc atctcgaccc gacttttagc 480
atcccccagg cgaatcatag ccatagcggc gattatcact gcaccgggaa tattgggtat 540
acgtctttta gcagcaagcc ggttactatc accgtgcagg gcggccatca tcatcatcat 600
cattaag 607

<210> SEQ ID NO 49
<211> LENGTH: 201
<212> TYPE: PRT

```
<213> ORGANISM: Homo sapiens
<220> FEATURE:
<223> OTHER INFORMATION: MalE signal - FcgRIIa(m11)-Del8 - 6His

<400> SEQUENCE: 49

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Thr Asn Val Leu
        35                  40                  45

Gln Glu Asp Ser Val Thr Leu Thr Cys Gln Ser Val Leu Trp Phe His
    50                  55                  60

Asn Gly Asn Leu Ile Pro Thr Gln Thr Gln Leu Thr Tyr Arg Phe Lys
65                  70                  75                  80

Ala Thr Ser Asn Asp Ser Gly Glu Tyr Thr Cys Gln Thr Gly Gln Thr
                85                  90                  95

Ser Leu Ser Asp Pro Val His Leu Thr Val Leu Ser Glu Trp Leu Val
            100                 105                 110

Leu Gln Pro Pro Arg Leu Glu Phe Gln Glu Gly Glu Thr Ile Met Leu
        115                 120                 125

Arg Cys His Ser Trp Lys Asp Lys Pro Leu Val Lys Val Thr Phe Phe
    130                 135                 140

Gln Asn Gly Lys Ser Gln Lys Phe Ser His Leu Asp Pro Thr Phe Ser
145                 150                 155                 160

Ile Pro Gln Ala Asn His Ser His Ser Gly Asp Tyr His Cys Thr Gly
                165                 170                 175

Asn Ile Gly Tyr Thr Ser Phe Ser Ser Lys Pro Val Thr Ile Thr Val
            180                 185                 190

Gln Gly Gly His His His His His His
        195                 200


<210> SEQ ID NO 50
<211> LENGTH: 604
<212> TYPE: DNA
<213> ORGANISM: Homo sapiens
<220> FEATURE:
<223> OTHER INFORMATION: DNA encoding MalE signal - FcgRIIa(m11)-Del9 -
      6His

<400> SEQUENCE: 50

atgaaaataa aaacaggtgc acgcatcctc gcattatccg cattaacgac gatgatgttt      60

tccgcctcgg ctctcgccat gggacaagcc gcagcgcctc caaaggcggt tctgaaactg     120

gagccgccgt ggaccaatgt gttgcaggaa gatagcgtga cgctgacctg ccaggtactg     180

tggtttcaca acggcaattt gatccccact caaacgcagc tgacgtaccg tttcaaagcc     240

accagtaacg attcgggcga atatacctgc cagacaggcc agaccagcct gtcggatcca     300

gtgcacctga ccgtgctgtc agaatggctg gtgctgcaac cgccgcgtct ggaatttcag     360

gaaggcgaaa ccataatgct gcgttgccac agctggaaag ataaaccgct ggtgaaggtc     420

acgttcttcc agaacgggaa gagccagaag ttctcccatc tcgacccgac ttttagcatc     480

ccccaggcga atcatagcca tagcggcgat tatcactgca ccgggaatat tgggtatacg     540

tcttttagca gcaagccggt tactatcacc gtgcagggcg gccatcatca tcatcatcat     600

taag                                                                  604
```

```
<210> SEQ ID NO 51
<211> LENGTH: 200
<212> TYPE: PRT
<213> ORGANISM: Homo sapiens
<220> FEATURE:
<223> OTHER INFORMATION: MalE signal - FcgRIIa(m11)-Del9 - 6His

<400> SEQUENCE: 51

Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Thr Asn Val Leu
        35                  40                  45

Gln Glu Asp Ser Val Thr Leu Thr Cys Gln Val Leu Trp Phe His Asn
    50                  55                  60

Gly Asn Leu Ile Pro Thr Gln Thr Gln Leu Thr Tyr Arg Phe Lys Ala
65                  70                  75                  80

Thr Ser Asn Asp Ser Gly Glu Tyr Thr Cys Gln Thr Gly Gln Thr Ser
                85                  90                  95

Leu Ser Asp Pro Val His Leu Thr Val Leu Ser Glu Trp Leu Val Leu
            100                 105                 110

Gln Pro Pro Arg Leu Glu Phe Gln Glu Gly Glu Thr Ile Met Leu Arg
        115                 120                 125

Cys His Ser Trp Lys Asp Lys Pro Leu Val Lys Val Thr Phe Phe Gln
    130                 135                 140

Asn Gly Lys Ser Gln Lys Phe Ser His Leu Asp Pro Thr Phe Ser Ile
145                 150                 155                 160

Pro Gln Ala Asn His Ser His Ser Gly Asp Tyr His Cys Thr Gly Asn
                165                 170                 175

Ile Gly Tyr Thr Ser Phe Ser Ser Lys Pro Val Thr Ile Thr Val Gln
            180                 185                 190

Gly Gly His His His His His His
        195                 200


<210> SEQ ID NO 52
<211> LENGTH: 601
<212> TYPE: DNA
<213> ORGANISM: Homo sapiens
<220> FEATURE:
<223> OTHER INFORMATION: DNA encoding MalE signal - FcgRIIa(m11)-Del10 -
      6His

<400> SEQUENCE: 52

atgaaaataa aaacaggtgc acgcatcctc gcattatccg cattaacgac gatgatgttt     60

tccgcctcgg ctctcgccat gggacaagcc gcagcgcctc caaaggcggt tctgaaactg    120

gagccgccgt ggaccaatgt gttgcaggaa gatagcgtga cgctgacctg cgtactgtgg    180

tttcacaacg gcaatttgat ccccactcaa acgcagctga cgtaccgttt caaagccacc    240

agtaacgatt cgggcgaata tacctgccag acaggccaga ccagcctgtc ggatccagtg    300

cacctgaccg tgctgtcaga atggctggtg ctgcaaccgc cgcgtctgga atttcaggaa    360

ggcgaaacca taatgctgcg ttgccacagc tggaaagata aaccgctggt gaaggtcacg    420

ttcttccaga acgggaagag ccagaagttc tcccatctcg acccgacttt tagcatcccc    480

caggcgaatc atagccatag cggcgattat cactgcaccg ggaatattgg gtatacgtct    540

tttagcagca agccggttac tatcaccgtg cagggcggcc atcatcatca tcatcattaa    600
```

-continued g 601

<210> SEQ ID NO 53
<211> LENGTH: 199
<212> TYPE: PRT
<213> ORGANISM: Homo sapiens
<220> FEATURE:
<223> OTHER INFORMATION: MalE signal - FcgRIIa(m11)-Del10 - 6His

<400> SEQUENCE: 53

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Met Gly Gln Ala Ala Ala
            20                  25                  30

Pro Pro Lys Ala Val Leu Lys Leu Glu Pro Pro Trp Thr Asn Val Leu
        35                  40                  45

Gln Glu Asp Ser Val Thr Leu Thr Cys Val Leu Trp Phe His Asn Gly
    50                  55                  60

Asn Leu Ile Pro Thr Gln Thr Gln Leu Thr Tyr Arg Phe Lys Ala Thr
65                  70                  75                  80

Ser Asn Asp Ser Gly Glu Tyr Thr Cys Gln Thr Gly Gln Thr Ser Leu
                85                  90                  95

Ser Asp Pro Val His Leu Thr Val Leu Ser Glu Trp Leu Val Leu Gln
            100                 105                 110

Pro Pro Arg Leu Glu Phe Gln Glu Gly Glu Thr Ile Met Leu Arg Cys
        115                 120                 125

His Ser Trp Lys Asp Lys Pro Leu Val Lys Val Thr Phe Phe Gln Asn
    130                 135                 140

Gly Lys Ser Gln Lys Phe Ser His Leu Asp Pro Thr Phe Ser Ile Pro
145                 150                 155                 160

Gln Ala Asn His Ser His Ser Gly Asp Tyr His Cys Thr Gly Asn Ile
                165                 170                 175

Gly Tyr Thr Ser Phe Ser Ser Lys Pro Val Thr Ile Thr Val Gln Gly
            180                 185                 190

Gly His His His His His His
        195
```